US009217006B2

(12) United States Patent
Parham et al.

(10) Patent No.: US 9,217,006 B2
(45) Date of Patent: Dec. 22, 2015

(54) MATERIALS FOR ORGANIC ELECTROLUMINESCENT DEVICES

(75) Inventors: Amir Hossain Parham, Frankfurt (DE); Arne Buesing, Frankfurt (DE); Anja Gerhard, Egelsbach (DE); Joachim Kaiser, Darmstadt (DE); Rocco Fortte, Frankfurt (DE)

(73) Assignee: Merck Patent GmbH, Darmstadt (DE)

( * ) Notice: Subject to any disclaimer, the term of this patent is extended or adjusted under 35 U.S.C. 154(b) by 637 days.

(21) Appl. No.: 13/001,863

(22) PCT Filed: Oct. 14, 2009

(86) PCT No.: PCT/EP2009/007360
§ 371 (c)(1),
(2), (4) Date: Dec. 29, 2010

(87) PCT Pub. No.: WO2010/054728
PCT Pub. Date: May 20, 2010

(65) Prior Publication Data
US 2011/0108822 A1  May 12, 2011

(30) Foreign Application Priority Data
Nov. 13, 2008 (DE) .................. 10 2008 057 051

(51) Int. Cl.
C09K 11/06 (2006.01)
H01L 51/54 (2006.01)
C07F 15/00 (2006.01)
H01L 51/00 (2006.01)
C09B 57/00 (2006.01)
C09B 57/10 (2006.01)
H01L 51/50 (2006.01)

(52) U.S. Cl.
CPC ........... *C07F 15/006* (2013.01); *C07F 15/0086* (2013.01); *C09B 57/00* (2013.01); *C09B 57/008* (2013.01); *C09B 57/10* (2013.01); *C09K 11/06* (2013.01); *H01L 51/0087* (2013.01); *C09K 2211/1029* (2013.01); *C09K 2211/1044* (2013.01); *C09K 2211/185* (2013.01); *H01L 51/5016* (2013.01); *Y02E 10/549* (2013.01)

(58) Field of Classification Search
CPC ........... H01L 51/5012; H01L 51/5016; H01L 51/0084; H01L 51/0087; C09K 11/06; C09K 2211/1029; C09K 2211/1044; C09K 2211/185; C07F 15/0086
See application file for complete search history.

(56) References Cited

U.S. PATENT DOCUMENTS

2002/0100906 A1\* 8/2002 Takiguchi et al. .............. 257/40
2003/0091862 A1\* 5/2003 Tokito et al. .................. 428/690
2005/0227112 A1\* 10/2005 Ise et al. ........................ 428/690
2006/0073359 A1\* 4/2006 Ise et al. ........................ 428/690
2006/0134461 A1\* 6/2006 Huo et al. ...................... 428/690
2006/0243966 A1 11/2006 Sotoyama et al.
2007/0075311 A1 4/2007 Okada
2007/0082284 A1 4/2007 Stoessel et al.

FOREIGN PATENT DOCUMENTS

| EP | 1683804 A2 | 7/2006 | |
|---|---|---|---|
| JP | 2008504880 | 5/1996 | |
| JP | 2002234894 A | 8/2002 | |
| JP | 2007123862 A | 5/2007 | |
| JP | 2007-161886 A * | 6/2007 | ............. C09K 11/06 |
| JP | 2007161886 A | 6/2007 | |
| WO | WO-9501410 A1 | 1/1995 | |
| WO | WO-2004/108857 A1 | 12/2004 | |
| WO | WO-2005/042550 A1 | 5/2005 | |

OTHER PUBLICATIONS

Pratihar, et al., "Palladium(II) Complexes of N-[2-pyridyl)methyliden]-α(or β)-Aminonaphthalene: Single Crystal X-ray Structure of Di-chloro-N-[{(2-pyridyl)methyliden}-β-aminonaphthalene]-palladium(II), Pd(β-NaiPy)Cl$_2$, Spectra and DFT, TD-DFT Study," Polyhedron, vol. 26, pp. 4328-4344 (2007).

Rose, et al., "A New Bis(1-naphthylimino)acenaphthene Compound and its Pd(II) and Zn(II) Complexes: Synthesis, Characterization, Solid-State Structures and Density Functional Theory Studies on the Syn and Anti Isomers," Inorg. Chem., vol. 47, No. 17, pp. 7734-7744 (2006).

Gourbatsis et al., "The Coordination Chemistry of N,N'-ethylenebis(2-acetylpyridine imine) and N,N'-ethylenebis(2-benzoylpyridine imine); Two Potentially Tetradentate Ligands Containing Four Nitrogen Atoms," Transition Met. Chem., vol. 15, pp. 300-308 (1990).

Castiñneiras et al., "Synthesis, Structural Characterization and Properties of the Palladium(II) and Platinum(II) Complexes of 2-{2-[(pyridin-2-yl)aminomethylene]hydrazono}-thiazolidin-4-one and the 3-Methyl Derivative," Z. Anorg. Allg. Chem., vol. 634, No. 12-13, pp. 2281-2290 (2008).

Pregosin, P.S., et al., "Reactions of Palladium(II) Cyclometallated Benzylideneaniline Schiff's Bases. Some Relative Rates for the Synthesis of *ortho*-Substituted Carbomethoxy Derivatives via CO Insertion", Journal of Organometallic Chemistry, vol. 273, No. 3, (1984), pp. 401-413.

(Continued)

Primary Examiner — Michael H Wilson
(74) Attorney, Agent, or Firm — Drinker Biddle & Reath LLP

(57) ABSTRACT

The present invention relates to transition-metal complexes of the general formula I or II, in particular as emitter molecules in organic electronic devices, to a layer and to an electronic device which comprise the compounds according to the invention, and to a process for the preparation of the compounds according to the invention.

21 Claims, No Drawings

(56) References Cited

OTHER PUBLICATIONS

Vincente, J., et al., "A new example of a Palladium-Assisted Aryl Rearrangement. Synthesis and Reactivity of (2,3,4-Trimethoxy-6-X-phenyl)palladium [X=CHO, CH=N($n$-$C_{10}H_{21}$), CH=$NC_6H_4(NH_2)$-2, C(O)Me] and (3,4,5-Trimethoxy-2-X-phenyl)palladium [X=CHO, CH=$NC_6H_4(NH_2)$-2] Complexes. Crystal and Molecular Structure of [Pd($K^3$-$C_6H\{CH=NC_6H_4(NH_2)$-2$\}$-6-$(OMe)_3$-2,3,4)($PPH_3$)]$CF_3SO_3$, [Pd($K^3$-$C_6H\{CH=NC_6H_4(NH_2)$-2$\}$-2-$(OMe)_3$-3,4,5)($PPH_3$)]$CF_3SO_3$, and [Pd($k^2$-$C_6H\{C(O)Me\}$-6-$(OMe)_3$-2,3,4)(2,9-dimethyl-1,10-phenanthroline)]$CF_3SO_3$", Organometallics, vol. 12, No. 10, (1993), pp. 4151-4160.

Vincente, J., et al., "Synthesis of Mono-, Di-, and Tri-arylgold(III) Complexes Using Organomercury Compounds—Synthesis of the First Aurated Schiff Bases", Chemische Berichte, vol. 129, No. 10, (1996), pp. 1301-1306.

\* cited by examiner

MATERIALS FOR ORGANIC ELECTROLUMINESCENT DEVICES

RELATED APPLICATIONS

This application is a national stage application (under 35 U.S.C. §371) of PCT/EP2009/007360, filed Oct. 14, 2009, which claims benefit of German Application No. 10 2008 057 051.6, filed Nov. 13, 2008.

The present invention relates to transition-metal complexes of the general formula I or II, in particular as emitter molecules in organic electronic devices, to a layer and an electronic device which comprise the compounds according to the invention, and to a process for the preparation of the compounds according to the invention.

Chelate complexes and organometallic compounds are used as functional materials in a number of applications of different types which can be ascribed to the electronics industry in the broadest sense. In the case of organic electroluminescent devices based on organic components (general description of the structure cf. U.S. Pat. Nos. 4,539,507 and 5,151,629) and individual components thereof, the organic light-emitting diodes (OLEDs), the market introduction has already taken place. In spite of the successes that have already been achieved, further improvements are still desirable here.

In recent years, organometallic complexes which exhibit phosphorescence instead of fluorescence have increasingly been under discussion (M. A. Baldo, S. Lamansky, P. E. Burrows, M. E. Thompson, S. R. Forrest, Appl. Phys. Lett., 1999, 75, 4-6). For theoretical spin-statistical reasons, an up to four-fold increase in energy and power efficiency is possible using organometallic compounds as phosphorescence emitters. The main conditions that should be mentioned here for practical use are, in particular, a long operating lifetime, high stability to temperature stresses and a low use and operating voltage in order to facilitate mobile applications.

Besides the individual specific weak points for each material, the class of known metal complexes has general weak points, which are described briefly below:

Many of the known metal complexes have low thermal stability (cf.: R. G. Charles, J. Inorg. Nucl. Chem., 1963, 25, 45). On vacuum deposition, this inevitably always results in the liberation of organic pyrolysis products, which, in some cases even in small amounts, considerably shorten the operating lifetime of OLEDs.

The strong interaction of the complex units in the solid, in particular in the case of planar complexes of $d^8$ metals, such as platinum(II), likewise causes aggregation of the complex units in the emitter layer if the degree of doping exceeds about 0.1%, which is the case in accordance with the current prior art. This aggregation results in the formation of so-called excimers or exciplexes on excitation (optical or electrical). These aggregates frequently have an unstructured, broad emission band, which makes the generation of pure primary colours (RGB) considerably more difficult or completely impossible. In general, the efficiency for this transition also drops.

In addition, it is evident from the above-said that the emission colour is highly dependent on the degree of doping, a parameter which can be controlled precisely only with considerable technical effort, in particular in large production plants.

Known in OLED technology are metal complexes of the group 10 transition metals (Ni, Pd, Pt) in which the central metal is bonded via two aromatic N atoms and two C atoms (WO 2004/108857, WO 2005/042550, WO 2005/042444, US 2006/0134461 A1) or two imine-like N atoms in combination with two phenolic O atoms (WO 2004/108857) or via two aromatic N atoms and two basic N atoms (WO 2004/108857). The known compounds have, inter alia, electroluminescence in the blue, red and green region of the electromagnetic spectrum.

Nevertheless, there is still a demand for further compounds which do not have the above-mentioned disadvantages and preferably exhibit electroluminescence in the blue, red and green region of the electromagnetic spectrum and in particular can also be employed in pure form as light-emitting layer.

The object of the invention was thus to provide compounds of this type.

Surprisingly, it has been found that complexes containing imine-like N atoms in combination with aromatic C atoms or olefinic C atoms in combination with aromatic N atoms achieve a long operating lifetime as phosphorescence emitters in OLEDs, and achieve high stability to temperature stresses and a low use and operating voltage by bridging these ligands.

The present invention provides in this respect a compound of the general formula I

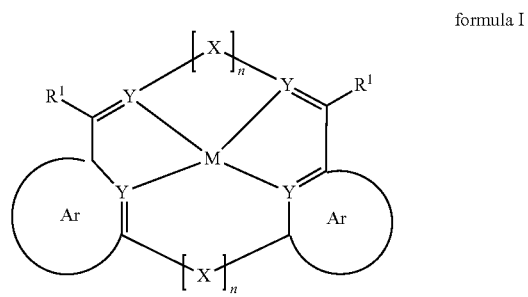

formula I where

M is a metal ion in oxidation state +2,

Ar is, identically or differently on each occurrence, an aromatic or heteroaromatic ring system, which may be substituted by one or more radicals R of any desired type, and the ring systems Ar may optionally be linked to one another by single bonds or any desired radicals R, Y is, identically or differently on each occurrence, C, N or P, with the proviso that always either two C atoms and two N atoms or two C atoms and two P atoms are bonded to the metal, X is, identically or differently on each occurrence, a divalent group selected from $B(R^1)$, $C(R^1)_2$, $Si(R^1)_2$, C=O, C=NR$^1$, C=C(R$^1)_2$, O, S, S=O, SO$_2$, N(R$^1$), P(R$^1$) and P(=O)R$^1$ or combinations thereof, or an aromatic or heteroaromatic ring system having 5 to 60 aromatic ring atoms, which may be substituted by one or more radicals R, or combinations thereof, $R^1$ is, identically or differently on each occurrence, any desired radical, n is on each occurrence, identically or differently, 0 or 1, where, for n=0, a hydrogen or a radical R or Ar is bonded instead of the X concerned.

The present invention furthermore provides a compound of the general formula II formula II

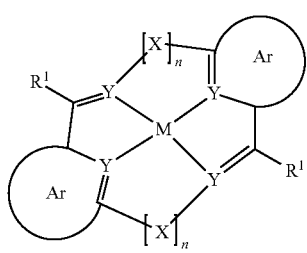

where

M is a metal ion in oxidation state +2,

Ar is, identically or differently on each occurrence, an aromatic or heteroaromatic ring system, which may be substituted by one or more radicals R of any desired type, and the ring systems Ar may optionally be linked to one another by single bonds or any desired radicals R, Y is, identically or differently on each occurrence, C, N or P, with the proviso that always either two C atoms and two N atoms or two C atoms and two P atoms are bonded to the metal, X is, identically or differently on each occurrence, a divalent group selected from $B(R^1)$, $C(R^1)_2$, $Si(R^1)_2$, $C=O$, $C=NR^1$, $C=C(R^1)_2$, O, S, $S=O$, $SO_2$, $N(R^1)$, $P(R^1)$ and $P(=O)R^1$ or combinations thereof, or an aromatic or heteroaromatic ring system having 5 to, 60 aromatic ring atoms, which may be substituted by one or more radicals R, or combinations thereof, $R^1$ is, identically or differently on each occurrence, any desired radical, n is, identically or differently on each occurrence, 0 or 1, where, for n=0, a hydrogen or a radical R or Ar is bonded instead of the X concerned.

In a preferred embodiment of the invention, in the compounds of the general formula I or II, Ar is, identically or differently on each occurrence, an aromatic or heteroaromatic ring system, which may be substituted by one or more radicals R of any desired type, and the ring systems Ar may optionally be linked to one another by single bonds or any desired radicals R, X is, identically or differently on each occurrence, a divalent group selected from

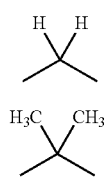 (i)

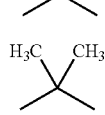 (ii)

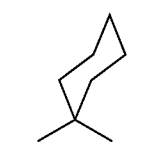 (iii)

 (iv)

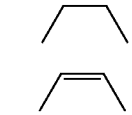 (v)

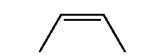 (vi)

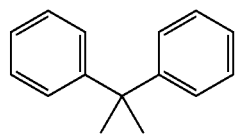 (vii)

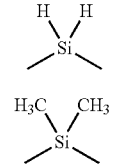 (viii)

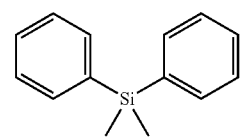 (viiii)

 (x)

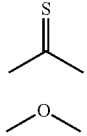 (xi)

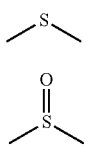 (xii)

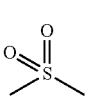 (xiii)

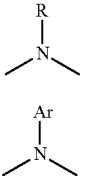 (xiv)

 (xv)

(xvi)

(xvii)

(xviii)

(xix)

(xx)

or combinations thereof;

or an aromatic or heteroaromatic ring system selected from

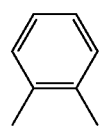 (xxi)

-continued

(xxii)

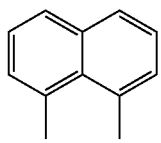
(xxiii)

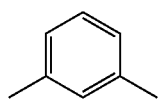
(xxiv)

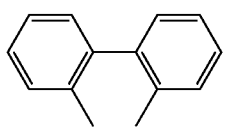
(xxv)

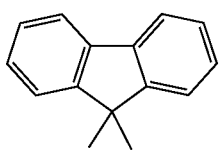
(xxvi)

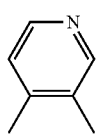
(xxvii)

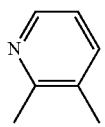
(xxviii)

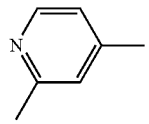
(xxix)

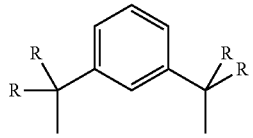
(xxx)

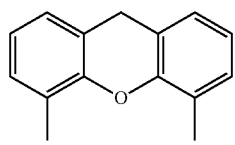
(xxxi)

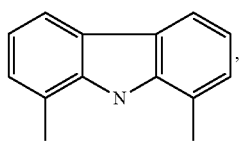
(xxxii)

which may be substituted by one or more radicals R, or combinations thereof;

R is, identically or differently on each occurrence, D, F, Cl, Br, I, $N(Ar^1)_2$, $N(R^2)_2$, CN, $NO_2$, $Si(R^2)_3$, $B(OR^2)_2$, $C(=O)Ar^1$, $C(=O)R^2$, $P(=O)(Ar^1)_2$, $P(=O)(R^2)_2$, $S(=O)Ar^1$, $S(=O)R^2$, $S(=O)_2Ar^1$, $S(=O)_2R^2$, $CR^2=CR^2Ar^1$, $OSO_2R^2$, a straight-chain alkyl, alkoxy or thioalkoxy group having 1 to 40 C atoms or a branched or cyclic alkyl, alkoxy or thioalkoxy group having 3 to 40 C atoms, each of which may be substituted by one or more radicals $R^2$, where one or more non-adjacent $CH_2$ groups may be replaced by $R^2C=CR^2$, $C≡C$, $Si(R^2)_2$, $Ge(R^2)_2$, $Sn(R^2)_2$, $C=O$, $C=S$, $C=Se$, $C=NR^2$, $P(=O)(R^2)$, SO, $SO_2$, $NR^2$, O, S or $CONR^2$ and where one or more H atoms may be replaced by D, F, Cl, Br, I, CN or $NO_2$, or an aromatic or heteroaromatic ring system having 5 to 60 aromatic ring atoms, which may in each case be substituted by one or more radicals $R^2$, or an aryloxy or heteroaryloxy group having 5 to 60 aromatic ring atoms, which may be substituted by one or more radicals $R^2$, or a combination of these systems, where two or more substituents R may also form a mono- or polycyclic aliphatic or aromatic ring system with one another, $Ar^1$ is, identically or differently on each occurrence, an aromatic or heteroaromatic ring system having 5 to 40 aromatic ring atoms, which may be substituted by one or more non-aromatic radicals R, $R^1$ is, identically or differently on each occurrence, H, D, F, $CF_3$, CN, an alkyl, alkoxy or thioalkoxy group having 1 to 40 C atoms or a branched or cyclic alkyl, alkoxy or thioalkoxy group having 3 to 40 C atoms, each of which may be substituted by one or more radicals $R^2$, where one or more non-adjacent $CH_2$ groups may be replaced by $R^2C=CR^2$, $C≡C$, $Si(R^2)_2$, $Ge(R^2)_2$, $Sn(R^2)_2$ and where one or more H atoms may be replaced by D, F, Cl, Br, I, CN or $NO_2$, or an aromatic or heteroaromatic ring system having 5 to 60 aromatic ring atoms, which may in each case be substituted by one or more radicals $R^2$, or an aryloxy or heteroaryloxy group having 5 to 60 aromatic ring atoms, which may be substituted by one or more radicals $R^2$, or a combination of these systems, where $R^1$ may also form a mono- or polycyclic aliphatic or aromatic ring system with R, $R^2$ is, identically or differently on each occurrence, H, D, F, CN or an aliphatic, aromatic and/or heteroaromatic hydrocarbon radical having 1 to 20 C atoms, in which, in addition, one or more H atoms may be replaced by F, where two or more substituents $R^2$ also form a mono- or polycyclic aliphatic or aromatic ring system with one another.

In a further preferred embodiment of the invention, M is equal to Pd or Pt. M is particularly preferably equal to Pt.

In still a further preferred embodiment of the invention, in the compounds of the general formula I or II, M is Pt, Ar is, identically or differently on each occurrence, an aromatic or heteroaromatic ring system having 5 to 10 aromatic ring atoms, which may be substituted by a plurality of radicals R, X is, identically or differently on each occurrence, a divalent group selected from

(i)

-continued
(ii) 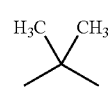
(iii) 
(iv) 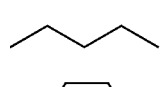
(v) 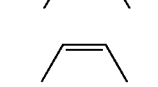
(vi) 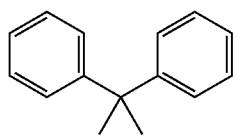
(vii) 
(viii) 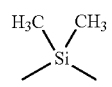
(ix) 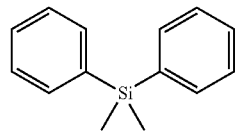
(x) 
(xi) 
(xii) 
(xiii) 
(xiv) 
(xv) 
(xvi) 
-continued
(xix) 
(xx) 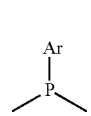
or combinations thereof, or an aromatic or heteroaromatic ring system having 5 to 15 aromatic ring atoms selected from
(xxi) 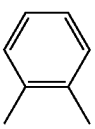
(xxii) 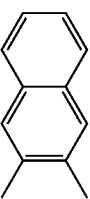
(xxiii) 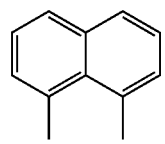
(xxiv) 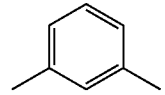
(xxv) 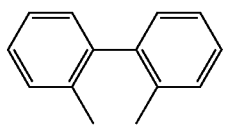
(xxvi) 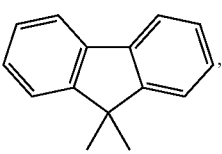

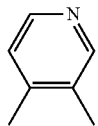
(xxvii)

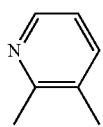
(xxviii)

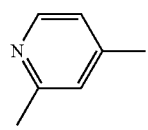
(xxix)

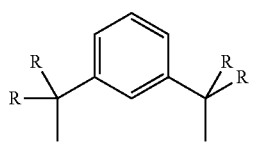
(xxx)

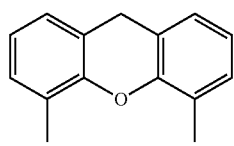
(xxxi)

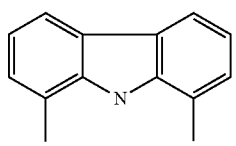
(xxxii)

which may be substituted by one or more radicals R, or combinations thereof,

Y is, identically or differently on each occurrence, C or N, with the proviso that two C atoms and two N atoms are always bonded to the metal, R is, identically or differently on each occurrence, $N(Ar^1)_2$, CN, a straight-chain alkyl group having 1 to 3 C atoms, or an aromatic or heteroaromatic ring system having 5 to 10 aromatic ring atoms, which may in each case be substituted by one or more radicals $R^2$, $R^1$ is, identically or differently on each occurrence, H, D, CN, an alkyl group having 1 to 10 C atoms, or an aromatic or heteroaromatic ring system having 5 to 10 aromatic ring atoms, which may in each case be substituted by one or more radicals $R^2$, $R^2$ is, identically or differently on each occurrence, H, F, CN or an aliphatic, aromatic and/or heteroaromatic hydrocarbon radical having 1 to 10 C atoms, where two or more substituents $R^2$ may also form a mono- or polycyclic aliphatic or aromatic ring system with one another, and $Ar^1$ is as defined above.

If the radicals and indices defined above occur a number of times within a compound, the radicals may, independently of one another on each occurrence, be identical or different, corresponding to the respective definition.

The two following compounds are excluded from the invention:

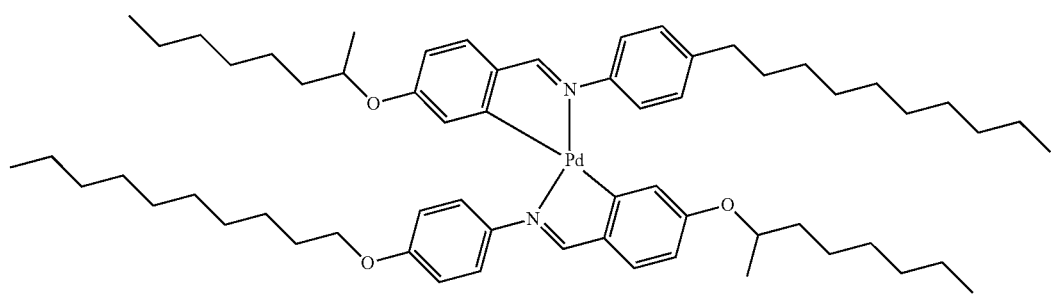

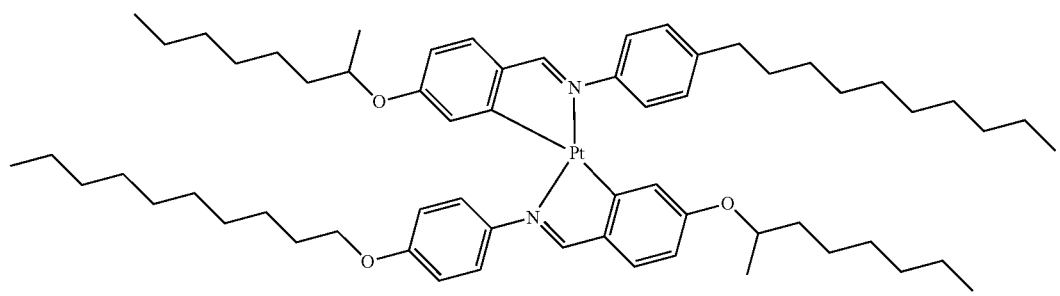

The following general definitions are furthermore used within this invention:

For the purposes of this invention, an aryl group contains 6 to 60 C atoms; for the purposes of this invention, a heteroaryl group contains 2 to 60 C atoms and at least one heteroatom, with the proviso that the sum of C atoms and heteroatoms is at least 5. The heteroatoms are preferably selected from N, O and/or S. An aryl group or heteroaryl group here is taken to mean either a simple aromatic ring, i.e. benzene, or a simple heteroaromatic ring, for example pyridine, pyrimidine, thiophene, etc., or a condensed (fused) aryl or heteroaryl group, for example naphthalene, anthracene, phenanthrene, quinoline, isoquinoline, carbazole, etc.

For the purposes of this invention, the group Ar in the general formulae I and II is particularly preferably benzene, naphthalene, pyridine, pyrimidine, pyrazine, pyridazine, quinoline, isoquinoline, furan, thiophene, pyrrole, benzofuran, benzothiophene or indole, where benzene, naphthalene, pyridine, quinoline and isoquinoline are most preferred.

Of the condensed aromatic groups, naphthalene, quinoline, benzothiophene, benzofuran and indole are preferred for the purposes of this invention; naphthalene and quinoline are particularly preferred.

For the purposes of this invention, an aromatic ring system contains 6 to 60 C atoms in the ring system. For the purposes of this invention, a heteroaromatic ring system contains 2 to 60 C atoms and at least one heteroatom in the ring system, with the proviso that the sum of C atoms and heteroatoms is at least 5. The heteroatoms are preferably selected from N, O and/or S. For the purposes of this invention, an aromatic or heteroaromatic ring system is intended to be taken to mean a system which does not necessarily contain only aryl or heteroaryl groups, but instead in which a plurality of aryl or heteroaryl groups may also be interrupted by a non-aromatic unit (preferably less than 10% of the atoms other than H), such as, for example, an sp$^3$-hybridised C, N or O atom. Thus, for example, systems such as 9,9'-spirobifluorene, 9,9-diarylfluorene, triarylamine, diaryl ether, stilbene, etc. are also intended to be taken to be aromatic ring systems for the purposes of this invention, as are systems in which two or more aryl groups are interrupted, for example, by a linear or cyclic alkyl group or by a silyl group.

An aromatic or heteroaromatic ring system having 5-60 aromatic ring atoms, which may also in each case be substituted by the above-mentioned radicals R$^1$ and which may be linked to the aromatic or heteroaromatic ring system via any desired positions, is taken to mean, in particular, groups derived from benzene, naphthalene, anthracene, benzanthracene, phenanthrene, pyrene, chrysene, perylene, fluoranthene, naphthacene, pentacene, benzopyrene, biphenyl, biphenylene, terphenyl, terphenylene, fluorene, spirobifluorene, dihydrophenanthrene, dihydropyrene, tetrahydropyrene, cis- or trans-indenofluorene, truxene, isotruxene, spirotruxene, spiroisotruxene, furan, benzofuran, isobenzofuran, dibenzofuran, thiophene, benzothiophene, isobenzothiophene, dibenzothiophene, pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, 1,5-diazaanthracene, 2,7-diazapyrene, 2,3-diazapyrene, 1,6-diazapyrene, 1,8-diazapyrene, 4,5-diazapyrene, 4,5,9,10-tetraazaperylene, pyrazine, phenazine, phenoxazine, phenothiazine, fluorubin, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole.

For the purposes of the present invention, an aliphatic hydrocarbon radical or an alkyl group, which may typically contain 1 to 40 or also 1 to 20 C atoms, and in which, in addition, individual H atoms or CH$_2$ groups may be substituted by the above-mentioned groups, is preferably taken to mean the radicals methyl, ethyl, n-propyl, i-propyl, n-butyl, i-butyl, s-butyl, t-butyl, 2-methylbutyl, n-pentyl, s-pentyl, cyclopentyl, n-hexyl, cyclohexyl, n-heptyl, cycloheptyl, n-octyl, cyclooctyl, 2-ethylhexyl, trifluoromethyl, pentafluoroethyl, 2,2,2-trifluoroethyl, ethenyl, propenyl, butenyl, pentenyl, cyclopentenyl, hexenyl, cyclohexenyl, heptenyl, cycloheptenyl, octenyl, cyclooctenyl, ethynyl, propynyl, butynyl, pentynyl, hexynyl, heptynyl or octynyl. An alkoxy group having 1 to 40 C atoms is preferably taken to mean methoxy, trifluoromethoxy, ethoxy, n-propoxy, i-propoxy, n-butoxy, i-butoxy, s-butoxy, t-butoxy, n-pentoxy, s-pentoxy, 2-methylbutoxy, n-hexoxy, cyclohexyloxy, n-heptoxy, cycloheptyloxy, n-octyloxy, cyclooctyloxy, 2-ethylhexyloxy, pentafluoroethoxy or 2,2,2-trifluoroethoxy. A thioalkyl group having 1 to 40 C atoms is taken to mean, in particular, methylthio, ethylthio, n-propylthio, i-propylthio, n-butylthio, i-butylthio, s-butylthio, t-butylthio, n-pentylthio, s-pentylthio, n-hexylthio, cyclohexylthio, n-heptylthio, cycloheptylthio, n-octylthio, cyclooctylthio, 2-ethylhexylthio, trifluoromethylthio, pentafluoroethylthio, 2,2,2-trifluoroethylthio, ethenylthio, propenylthio, butenylthio, pentenylthio, cyclopentenylthio, hexenylthio, cyclohexenylthio, heptenylthio, cycloheptenylthio, octenylthio, cyclooctenylthio, ethynylthio, propynylthio, butynylthio, pentynylthio, hexynylthio, heptynylthio or octynylthio. In general, alkyl, alkoxy or thioalkyl groups in accordance with the present invention may be straight-chain, branched or cyclic, where one or more non-adjacent CH$_2$ groups may be replaced by R$^1$C=CR$^1$, C≡C, Si(R$^1$)$_2$, Ge(R$^1$)$_2$, Sn(R$^1$)$_2$, C=O, C=S, C=Se, C=NR$^1$, P(=O) (R$^1$), SO, SO$_2$, NR$^1$, O, S or CONR$^1$; furthermore, one or more H atoms may also be replaced by F, Cl, Br, I, CN or NO$_2$, preferably F, Cl or CN, furthermore preferably F or Cl, particularly preferably F.

Preferred embodiments of the compounds of the formulae I and II are the following general formulae III and IV:

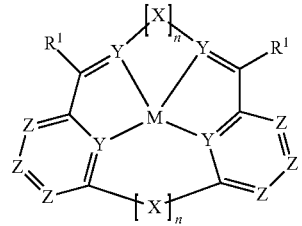

formula III

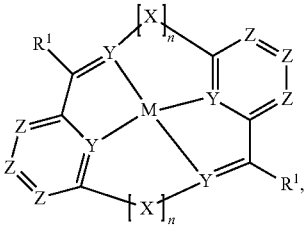

formula IV where M, X, Y, R and R$^1$ have the above-mentioned meanings and Z stands, identically or differently on each occurrence, for CR or N, particularly preferably for CR.

Besides the preferred compounds mentioned above, the compounds shown in Table 1 below are furthermore particularly preferred:

TABLE 1
Compounds according to the invention
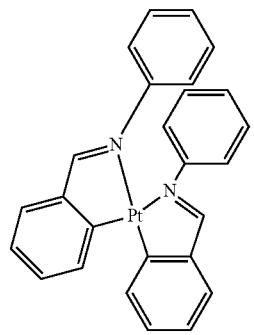
1
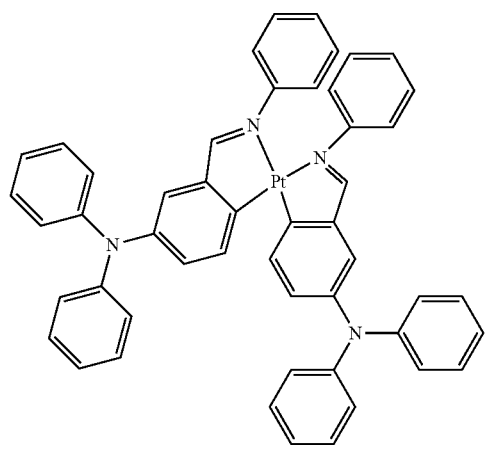
2
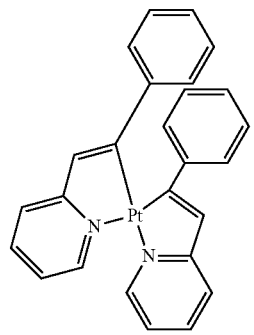
3

TABLE 1-continued
Compounds according to the invention
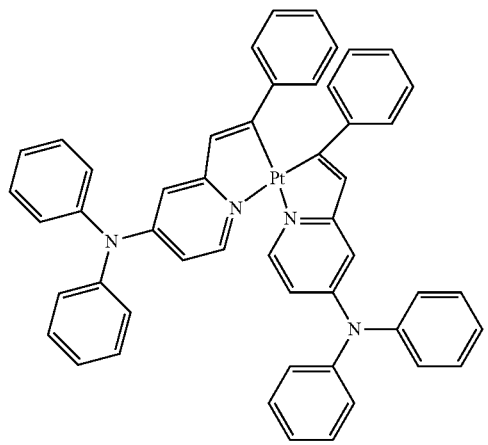
4
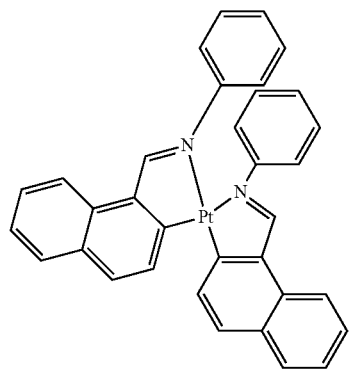
5
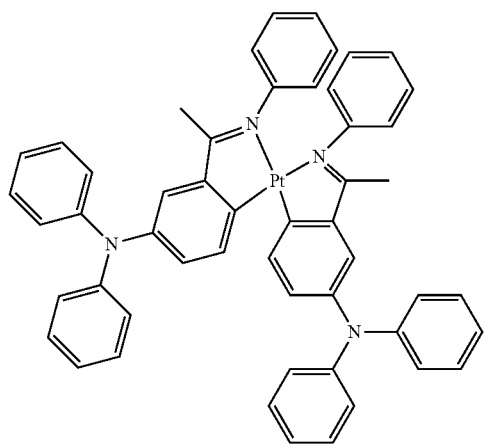
6

TABLE 1-continued
Compounds according to the invention
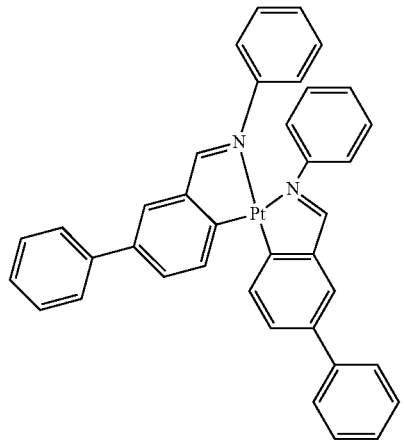
7
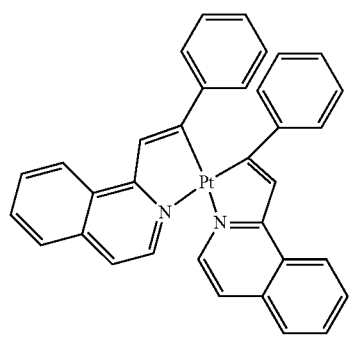
8
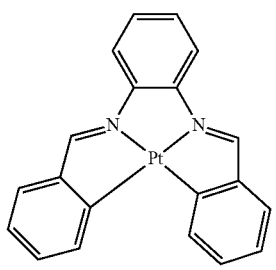
9
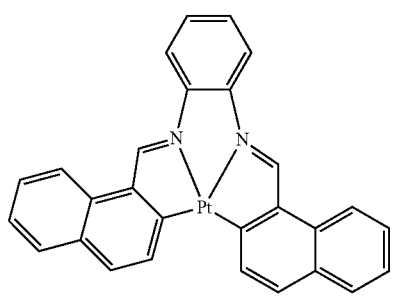
10

TABLE 1-continued
Compounds according to the invention
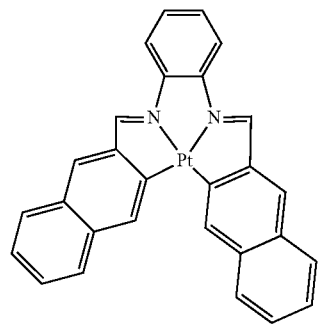
11
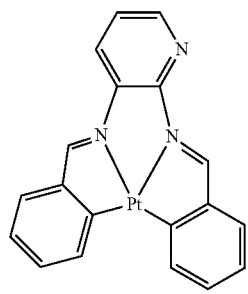
12
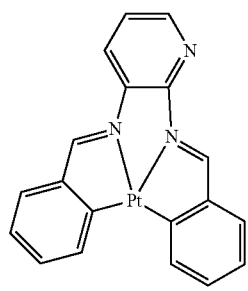
13
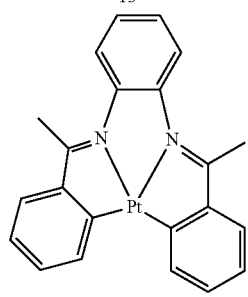
14

TABLE 1-continued
Compounds according to the invention
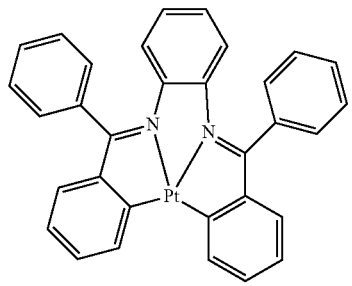
15
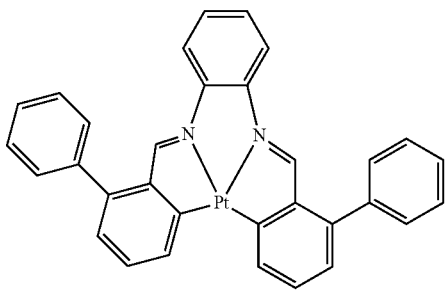
16
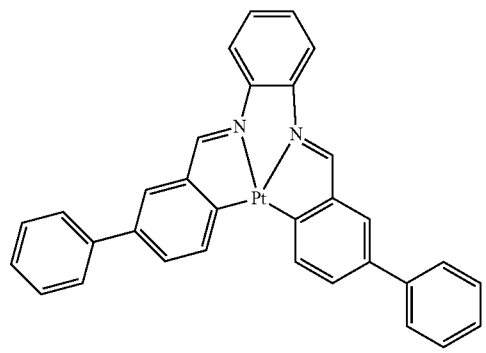
17
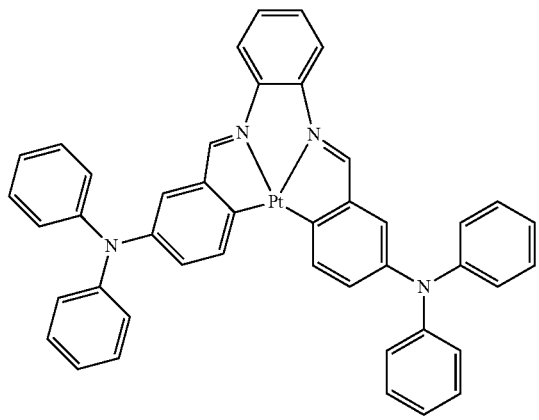
18

TABLE 1-continued
Compounds according to the invention
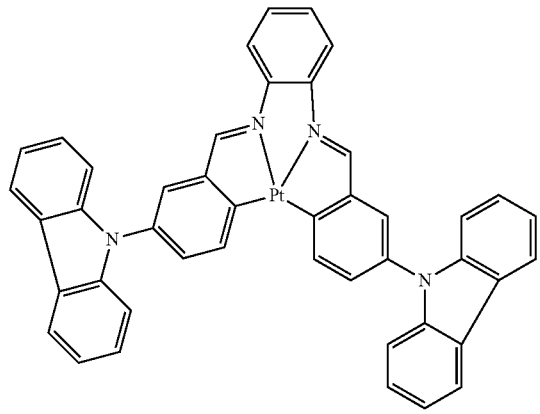
19
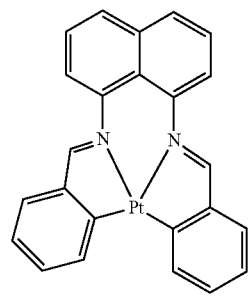
20
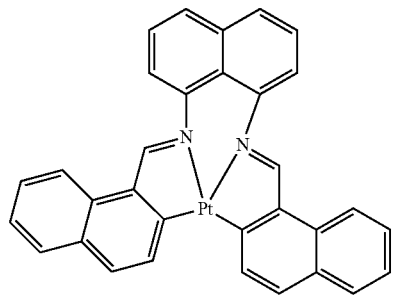
21
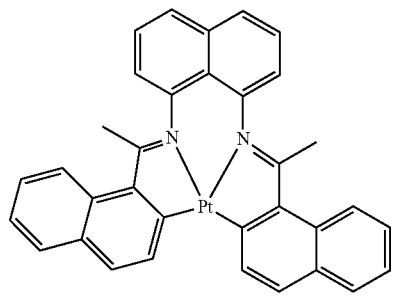
22

TABLE 1-continued
Compounds according to the invention
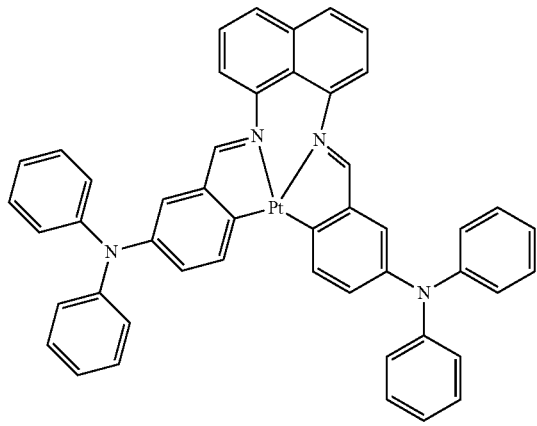
23
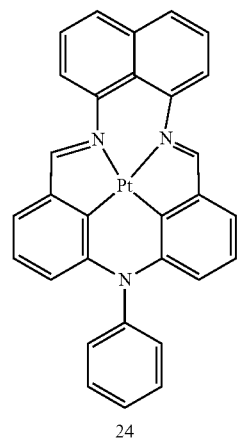
24
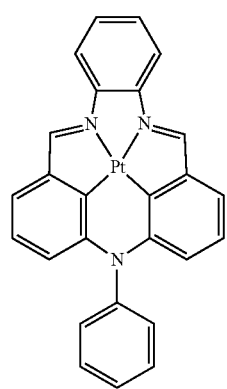
25

TABLE 1-continued
Compounds according to the invention
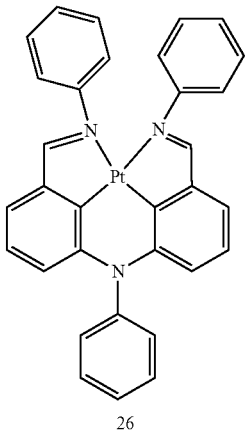
26
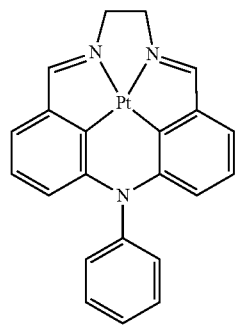
27
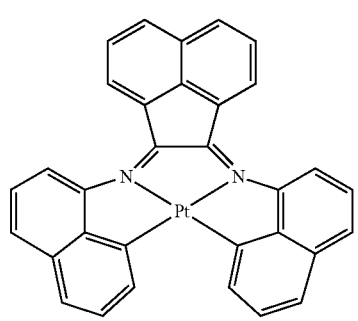
28
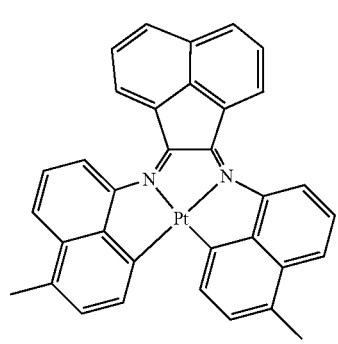
29

TABLE 1-continued
Compounds according to the invention
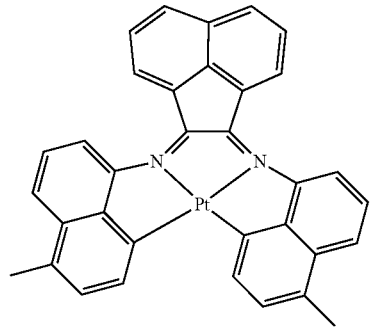
30
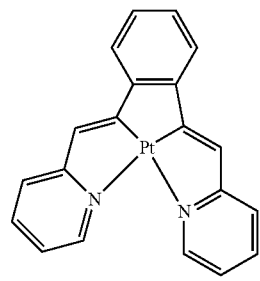
31
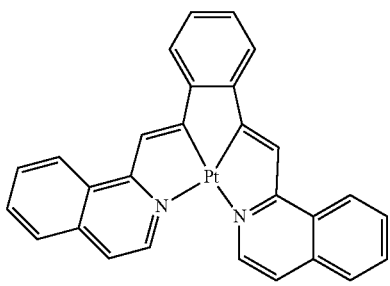
32
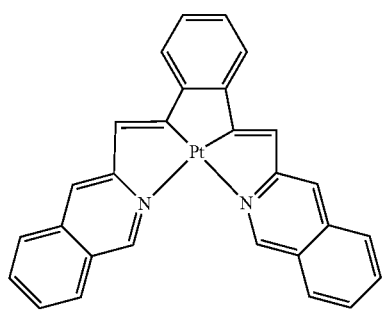
33

TABLE 1-continued
Compounds according to the invention
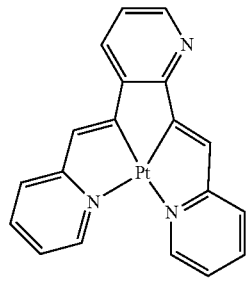
34
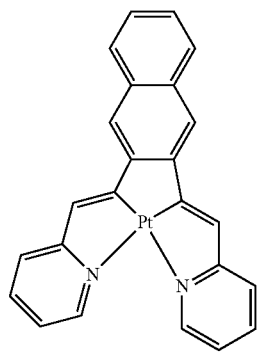
35
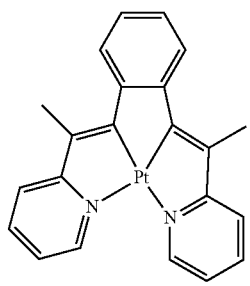
36
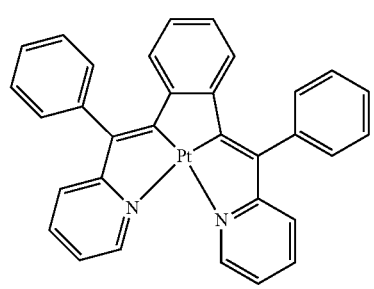
37

TABLE 1-continued
Compounds according to the invention
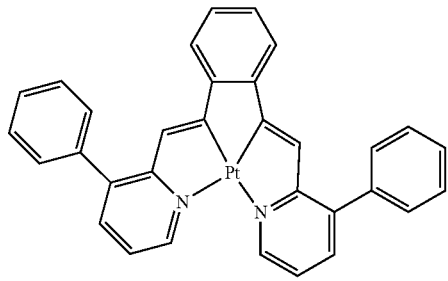
38
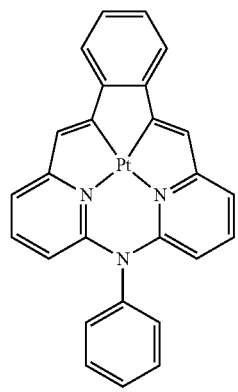
39
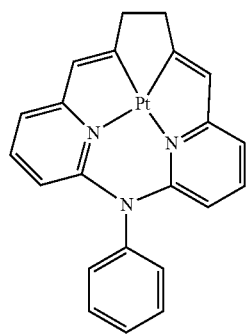
40
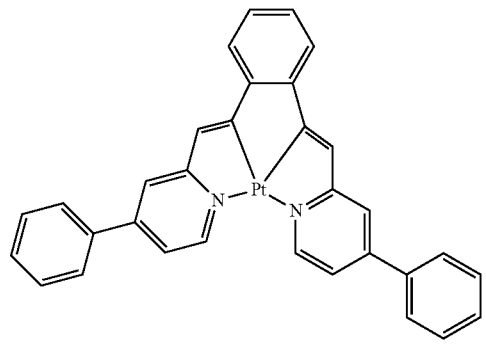
41

TABLE 1-continued
Compounds according to the invention
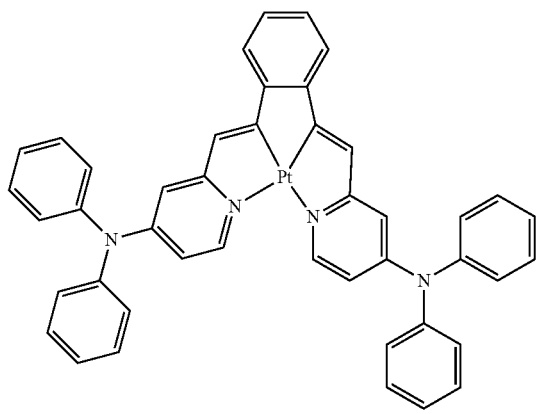
42
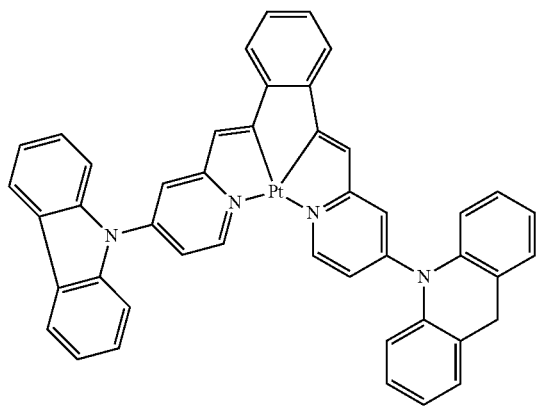
43
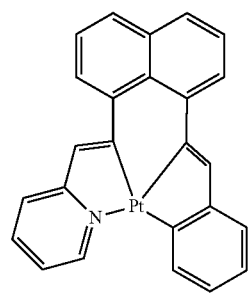
44
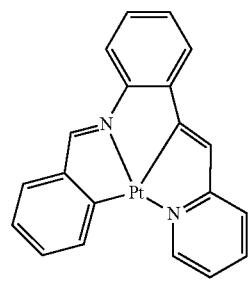
45

TABLE 1-continued
Compounds according to the invention
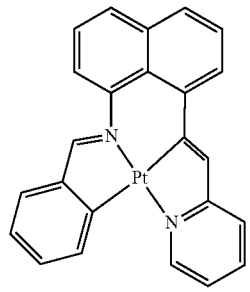
46
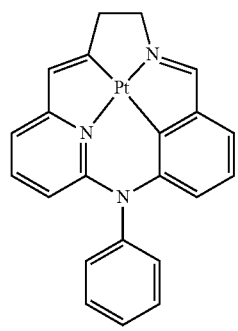
47
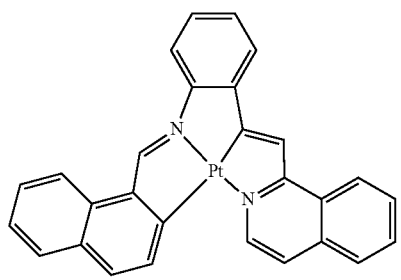
48
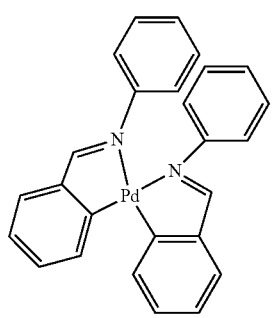
49

TABLE 1-continued
Compounds according to the invention
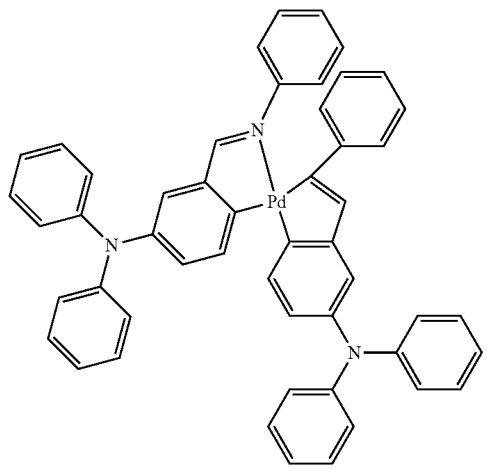
50
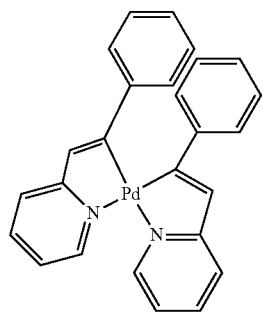
51
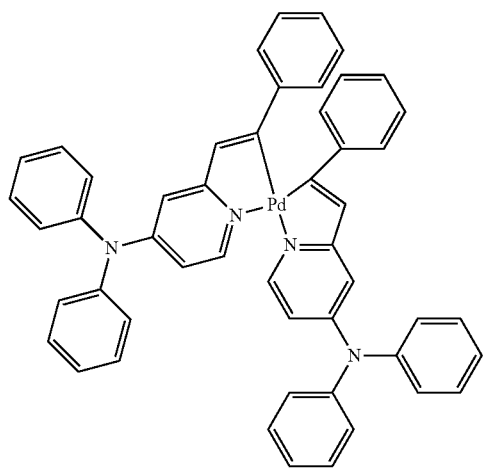
52

TABLE 1-continued
Compounds according to the invention
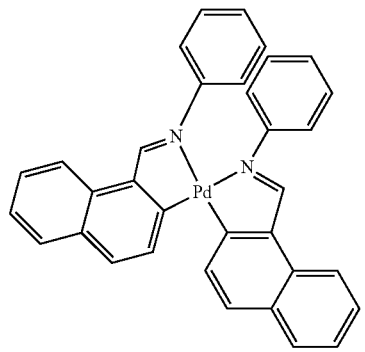
53
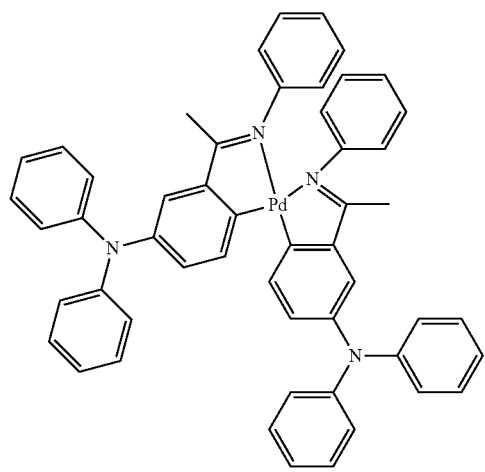
54
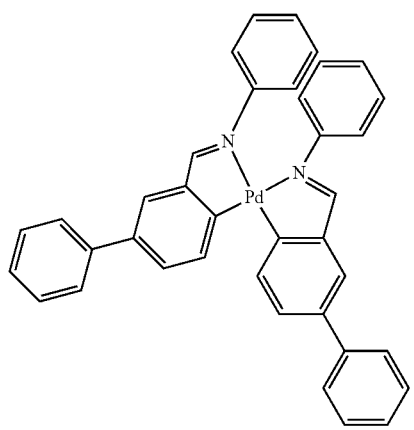
55

TABLE 1-continued
Compounds according to the invention
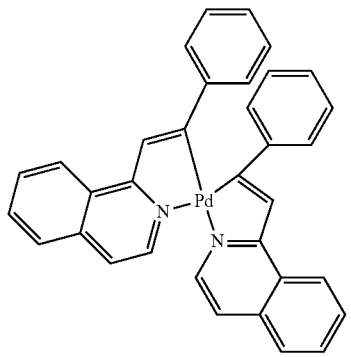
56
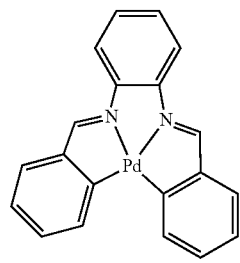
57
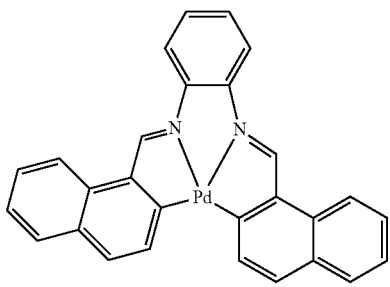
58
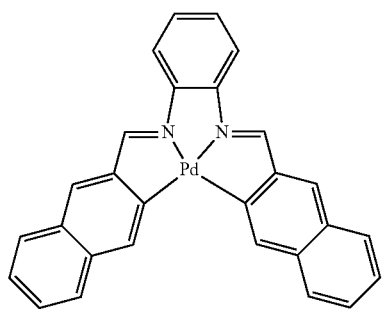
59

TABLE 1-continued
Compounds according to the invention
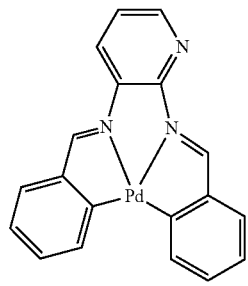
60
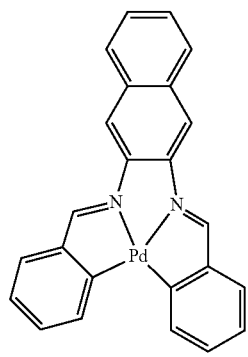
61
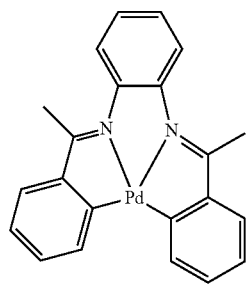
62
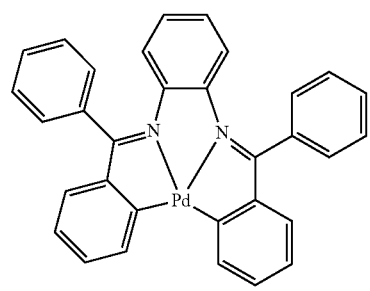
63

TABLE 1-continued
Compounds according to the invention
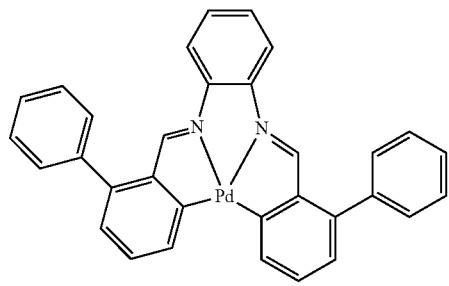
64
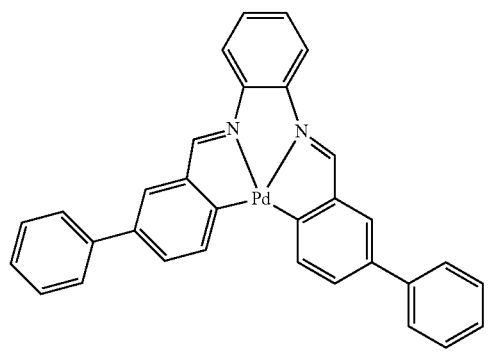
65
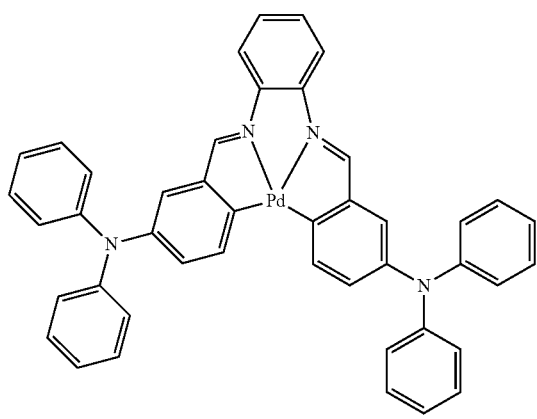
66
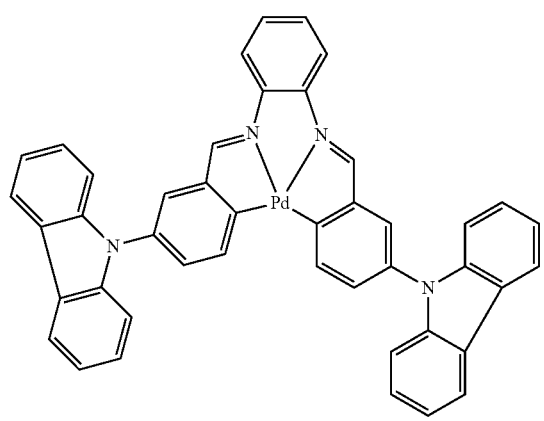
67

TABLE 1-continued
Compounds according to the invention
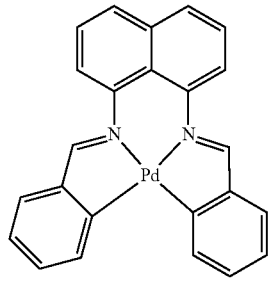
68
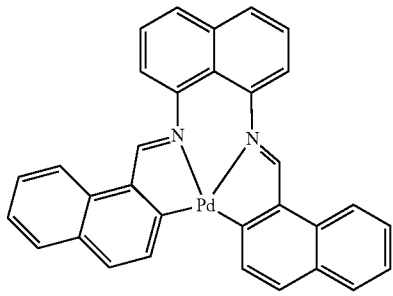
69
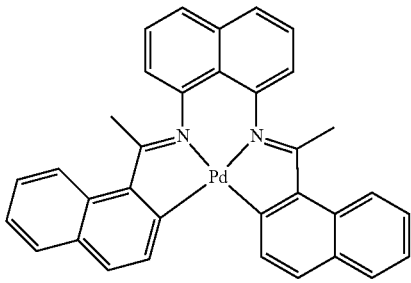
70
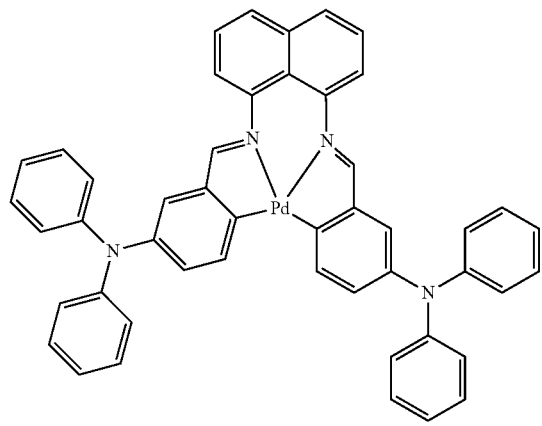
71

TABLE 1-continued
Compounds according to the invention
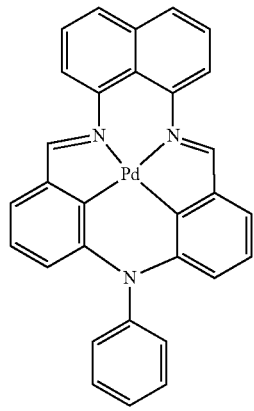
72
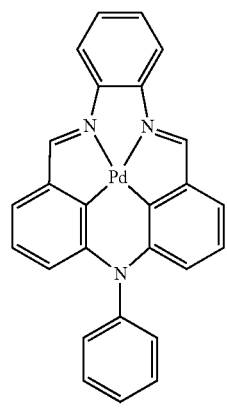
73
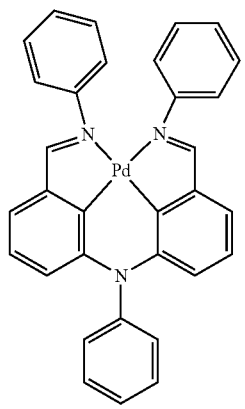
74

TABLE 1-continued
Compounds according to the invention
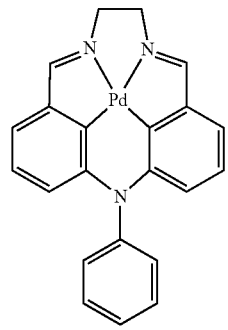
75
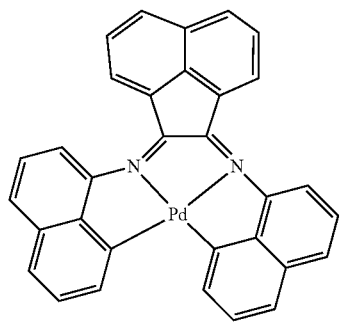
76
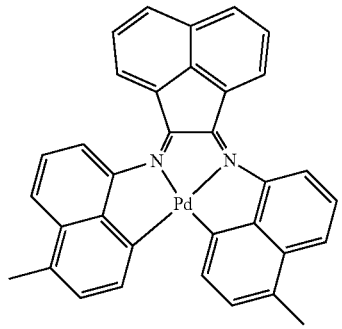
77
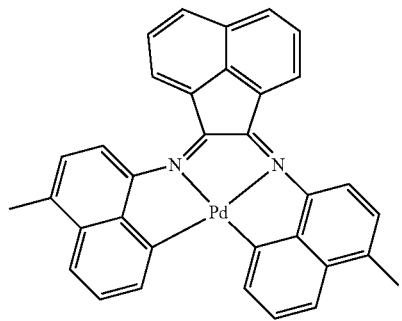
78

TABLE 1-continued
Compounds according to the invention
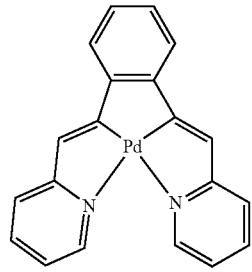
79
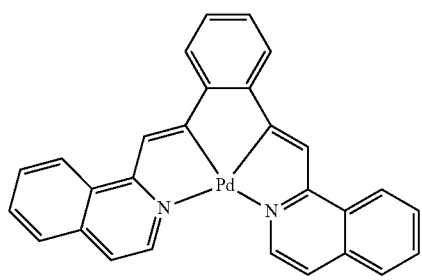
80
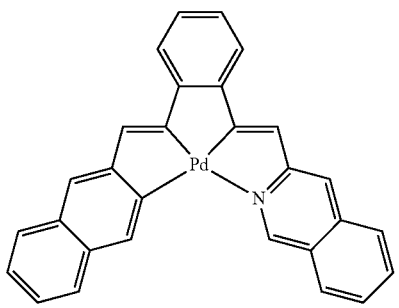
81
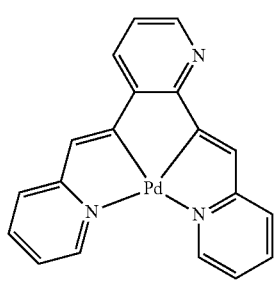
82

TABLE 1-continued
Compounds according to the invention
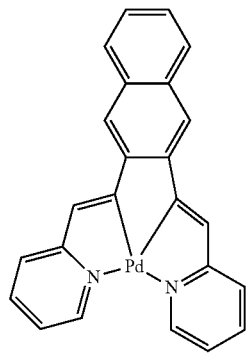
83
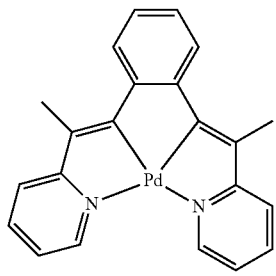
84
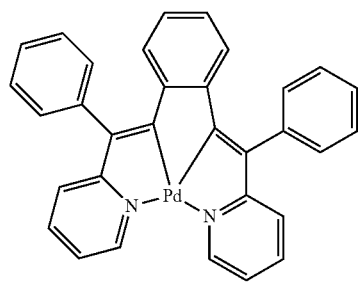
85
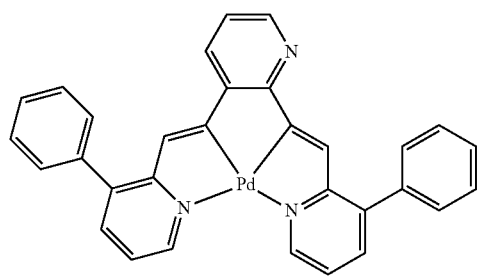
86

TABLE 1-continued
Compounds according to the invention
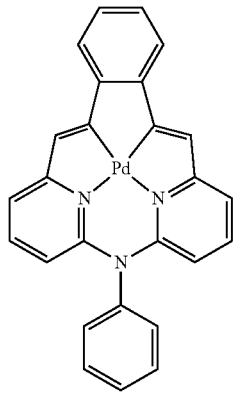
87
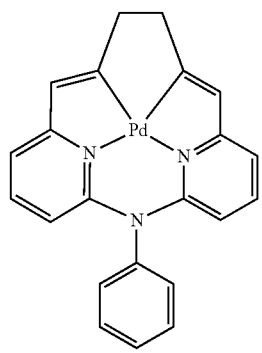
88
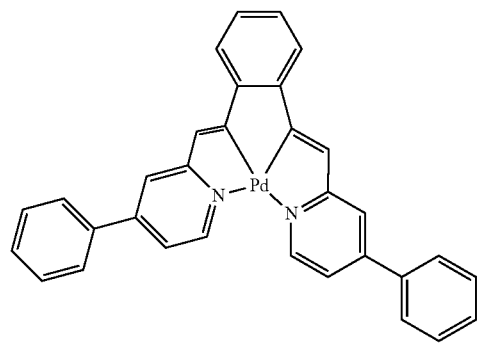
89

TABLE 1-continued
Compounds according to the invention
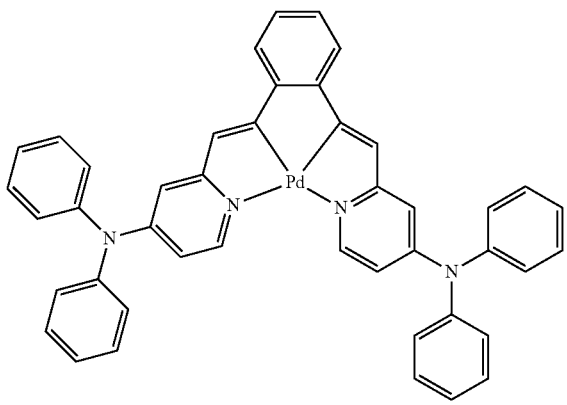
90
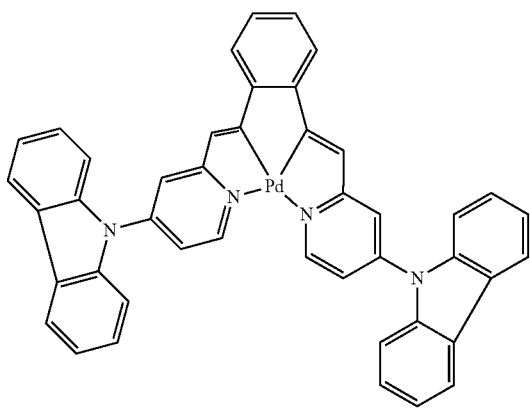
91
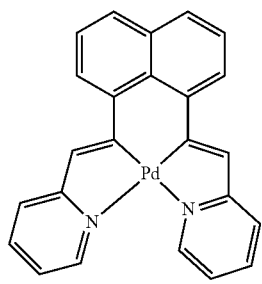
92
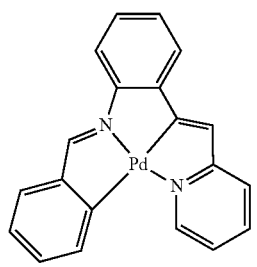
93

TABLE 1-continued
Compounds according to the invention
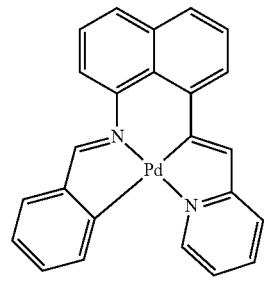
94
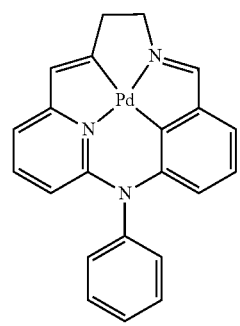
95
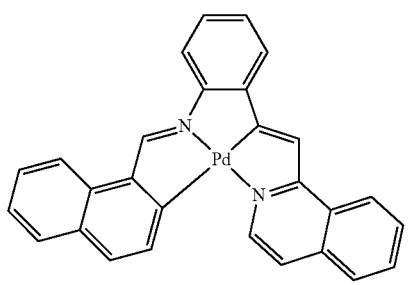
96
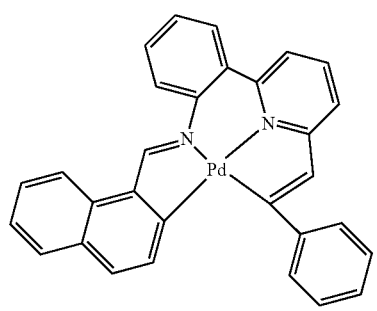
97

TABLE 1-continued
Compounds according to the invention
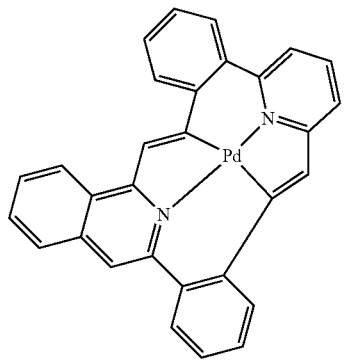
98
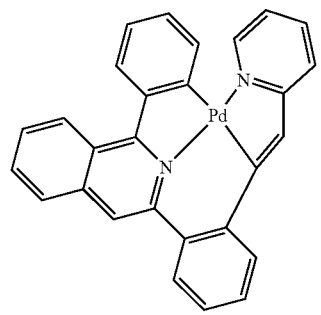
99
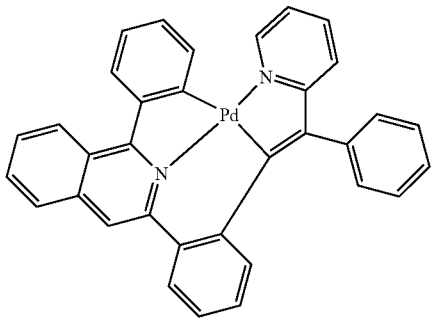
100
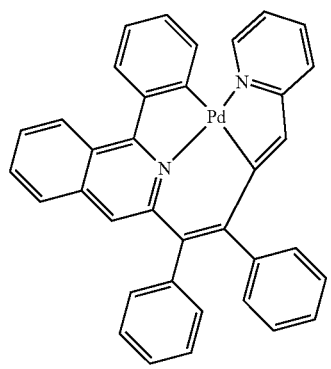
101

TABLE 1-continued
Compounds according to the invention
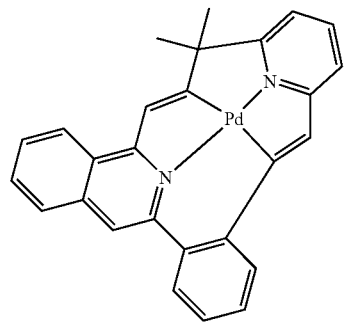
102
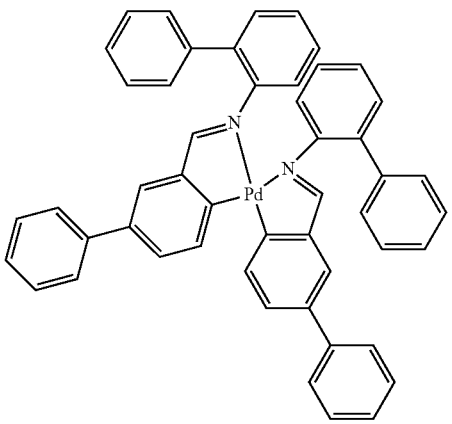
103
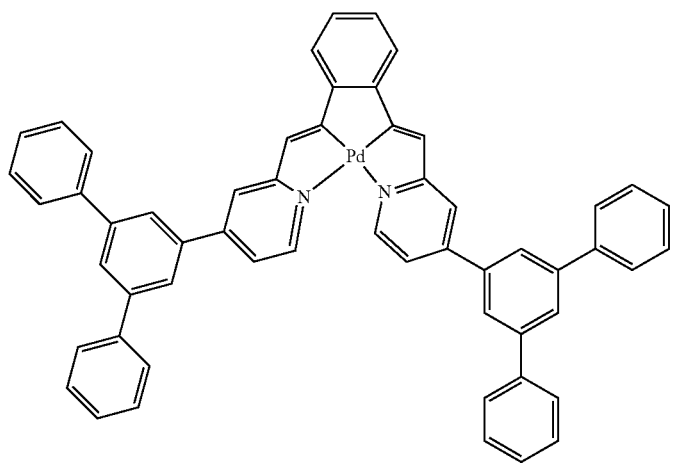
104

TABLE 1-continued

Compounds according to the invention

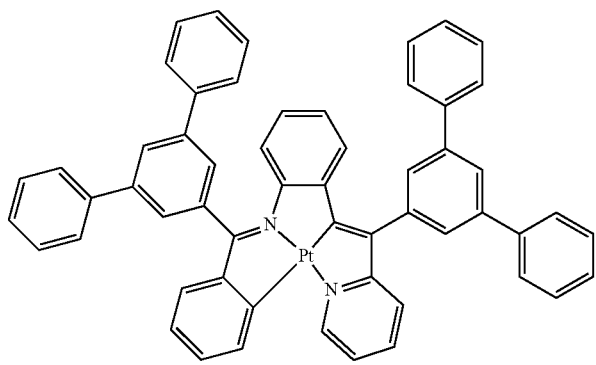

105

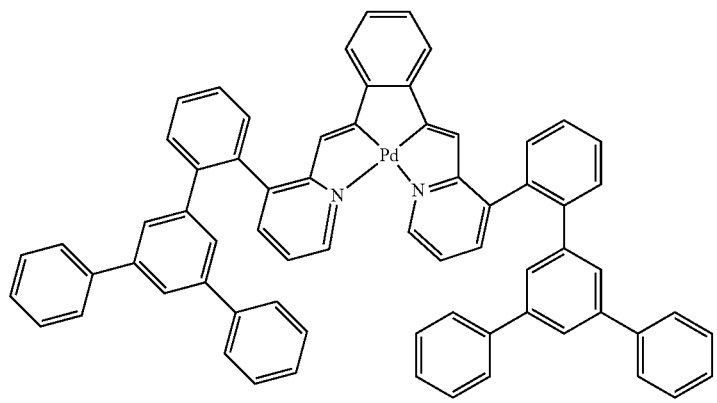

106

The compounds according to the invention are preferably square-planar complexes which contain a tetracoordinated metal ion in oxidation state +2. The metal is preferably selected from metals from group 10 of the Periodic Table of the Elements, in particular Pd and Pt. The compounds according to the invention show triplet emission and have a very good lifetime, high efficiency, high stability to temperature stresses and a high glass transition temperature Tg.

The invention also relates to a process for the preparation of a compound of the general formula I or II

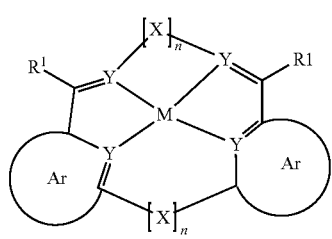

formula I

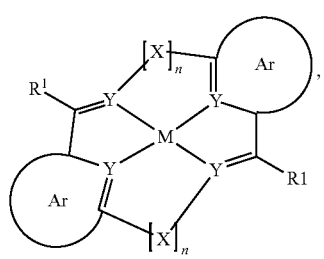

formula II where M, X, Y, Ar, R, $R^1$, $R^2$ and n have the meaning defined above.

The compounds of the formula I or II according to the invention can be prepared by synthetic steps generally known to the person skilled in the art.

The starting point for the ligand synthesis can be, for example, N-phenylbenzaldimine (Tetrahedron Lett. 2007, 48(40), 7177-7180), N,N'-dibenzylidene-o-phenylenediamine (J. Chem. Res. 2006, (1), 1-2), N,N'-bis(2-naphthalenylmethylene)-1,2-benzenediaminediene (J. Indian Chem.

Soc. 2002, 79(6), 502-504) or N,N'-di(benzylidene)-1,8-diaminonaphthalene (Toxicological and Environmental Chemistry 2006, 88(4), 579-586).

A first step involves the synthesis of the corresponding ligands, which are combined in a further step to give the desired ligand system. A reaction is subsequently carried out with the corresponding metal (such as, for example, Pt or Pd), which is usually employed as a solution of a suitable metal salt, for example $K_2PtCl_4$ or $K_2PdCl_4$.

A general synthetic procedure for the preparation of the metal complexes of the formula I or II is depicted in methods (A) and (B). The central metal Pt here can be replaced, for example, by Pd in analogous reactions.

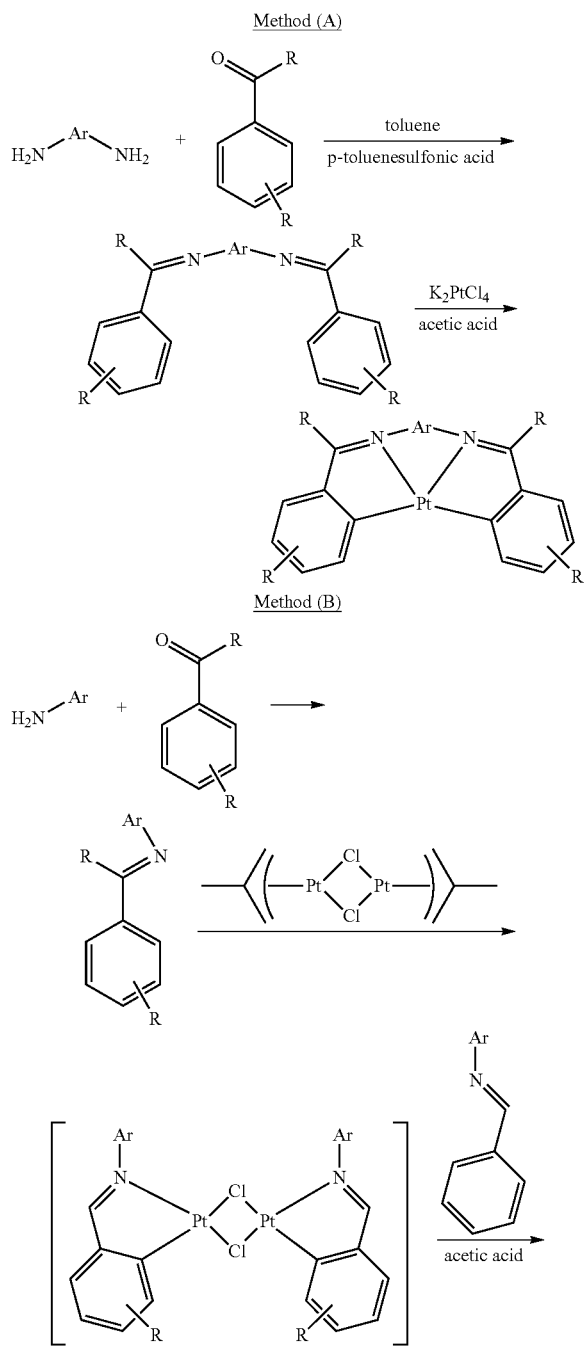

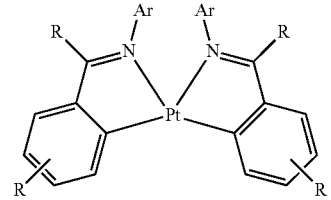

Compounds of the formula (II) can also be prepared analogously.

The invention also relates to the use of the compounds according to the invention in an organic electronic device, in particular as emitting compound. The electronic device used in accordance with the invention can be organic electroluminescent devices (OLEDs) or polymeric electroluminescent devices (PLEDs), organic integrated circuits (O-ICs), organic field-effect transistors (O-FETs), organic thin-film transistors (O-TFTs), organic light-emitting transistors (O-LETs), organic solar cells (O-SCs), organic optical detectors, organic photoreceptors, organic field-quench devices (O-FQDs), light-emitting electrochemical cells (LECs) or organic laser diodes (O-lasers), but in particular organic electroluminescent devices (=organic light-emitting diodes, OLEDs, PLEDs).

The invention also relates to the use of the compounds according to the invention as charge-transport material and/or charge-injection material, preferably in a corresponding layer. This can be either a hole-transport layer, hole-injection layer, electron-transport layer or electron-injection layer. The use as charge-blocking material is also possible.

The invention likewise relates to organic electronic devices, such as, for example, organic electroluminescent devices or polymeric electroluminescent devices (OLEDs, PLEDs), organic integrated circuits (O-ICs), organic field-effect transistors (O-FETs), organic thin-film transistors (O-TFTs), organic light-emitting transistors (O-LETs), organic solar cells (O-SCs), organic optical detectors, organic photoreceptors, organic field-quench devices (O-FQDs), light-emitting electrochemical cells (LECs) or organic laser diodes (O-lasers), but in particular organic electroluminescent devices (=organic light-emitting diodes, OLEDs, PLEDs), comprising one or more compounds of the formula I or II, as defined above. The organic electronic device here comprises an anode, cathode and at least one layer which comprises at least one organic or organometallic compound. However, the device may also comprise inorganic materials.

The compound of the formula I or II is preferably present within one layer in the electronic device.

The invention thus also relates to a layer comprising a compound of the formula I or II, as defined above.

The organic electroluminescent device comprises a cathode, anode and at least one emitting layer. Apart from these layers, it may also comprise further layers, for example in each case one or more hole-injection layers, hole-transport layers, hole-blocking layers, electron-transport layers, electron-injection layers, exciton-blocking layers and/or charge-generation layers (IDMC 2003, Taiwan; Session 21 OLED (5), T. Matsumoto, T. Nakada, J. Endo, K. Mori, N. Kawamura, A. Yokoi, J. Kido, *Multiphoton Organic EL Device Having Charge Generation Layer*). It is likewise possible that interlayers, which have, for example, an exciton-blocking function, are introduced between two emitting layers. However, it should be pointed out that each of these layers does not necessarily have to be present. These layers may comprise compounds of the general formula I or II, as defined above.

In a preferred embodiment of the invention, the compound of the formula I or II is employed as emitting compound in an emitting layer or as charge-transport compound in a charge-transport layer. The organic electroluminescent device here may comprise one emitting layer or a plurality of emitting layers, where at least one emitting layer comprises at least one cornpound of the formula I or II, as defined above. If a plurality of emission layers are present, these preferably have a plurality of emission maxima between 380 nm and 750 nm, resulting overall in white emission, i.e. various emitting compounds which are able to fluoresce or phosphoresce are used in the emitting layers. Particular preference is given to three-layer systems, where the three layers exhibit blue, green and orange or red emission (for the basic structure, see, for example, WO 05/011013). The device may furthermore comprise a plurality of charge-transport layers.

If the compound of the formula I or II is employed as emitting compound in an emitting layer, it is preferably employed in combination with one or more compounds functioning as matrix. In these cases, the mixture comprising the compound of the formula I or II and the matrix material comprises between 1 and 99% by weight, preferably between 2 and 90% by weight, particularly preferably between 3 and 40% by weight, in particular between 5 and 15% by weight, of the compound of the formula I or II, based on the entire mixture comprising emitter and matrix material. Correspondingly, the mixture comprises between 99 and 1% by weight, preferably between 98 and 10% by weight, particularly preferably between 97 and 60% by weight, in particular between 95 and 85% by weight, of the matrix material, based on the entire mixture comprising emitter and matrix material.

Preferred matrix materials are aromatic ketones, aromatic phosphine oxides or aromatic sulfoxides or sulfones, for example in accordance with WO 04/013080, WO 04/093207, WO 06/005627 or the unpublished application DE 102008033943.1, triarylamines, carbazole derivatives, for example CBP (N,N-biscarbazolylbiphenyl) or the carbazole derivatives disclosed in WO 05/039246, US 2005/0069729, JP 2004/288381, EP 1205527 or WO 08/086,851, indolocarbazole derivatives, for example in accordance with WO 07/063,754 or WO 08/056,746, azacarbazole derivatives, for example in accordance with EP 1617710, EP 1617711, EP 1731584, JP 2005/347160, bipolar matrix materials, for example in accordance with WO 07/137,725, silanes, for example in accordance with WO 05/111172, azaboroles or boronic esters, for example in accordance with WO 06/117052, triazine derivatives, for example in accordance with the unpublished application DE 102008036982.9, WO 07/063,754 or WO 08/056,746, zinc complexes, for example in accordance with EP 652273 or WO 09/062,578, or diazasilole or tetraazasilole derivatives, for example in accordance with the unpublished application DE 02008056688.8.

A further preferred embodiment of the invention is the use of the compound of the formula I or II as emitter material in combination with two or more different matrix materials. Suitable matrix materials in these cases are the preferred compounds mentioned above.

Preference is furthermore given to an organic electroluminescent device in which one or more layers are applied by means of a sublimation process, in which the materials are vapour-deposited in vacuum sublimation units at a pressure below $10^{-5}$ mbar, preferably below $10^{-6}$ mbar, particularly preferably below $10^{-7}$ mbar.

Preference is likewise given to an organic electroluminescent device, characterised in that one or more layers are applied by means of the OVPD (organic vapour phase deposition) process or with the aid of carriergas sublimation, in which the materials are applied at a pressure of between $10^{-5}$ mbar and 1 bar. A special case of this process is the OVJP (organic vapour jet printing) process, in which the materials are applied directly through a nozzle and thus structured (for example M. S. Arnold et al., *Appl. Phys. Lett.* 2008, 92, 053301).

Preference is furthermore given to an organic electroluminescent device, characterised in that one or more layers are produced from solution, such as, for example, by spin coating, or by means of any desired printing process, such as, for example, screen printing, flexographic printing or offset printing, but particularly preferably LITI (light induced thermal imaging, thermal transfer printing) or ink-jet printing. Soluble compounds, which are obtained, for example, by suitable substitution, are necessary for this purpose.

These processes are generally known to the person skilled in the art and can be applied by him without problems to organic electroluminescent devices comprising compounds of the formula I or II, as defined above.

The compounds according to the invention described above, in particular compounds which are substituted or functionalised by reactive groups, can be used as monomers for the preparation of corresponding oligomers, dendrimers or polymers.

The invention therefore furthermore relates to oligomers, polymers or dendrimers comprising one or more compounds of the formula I or II, as defined above, where one or more bonds are present from the compounds of the formula I or II to the polymer, oligomer or dendrimer. Depending on the linking of the compound of the formula I or II, the complex therefore forms a side chain of the oligomer or polymer or is linked in the main chain. The polymers, oligomers or dendrimers may be conjugated, partially conjugated or non-conjugated. The oligomers or polymers may be linear, branched or dendritic.

For the preparation of the oligomers or polymers, the functionalised compounds of the formula I or II are homopolymerised or copolymerised with further monomers. Preference is given to copolymers, where the cornpounds of the formula I or II are preferably present to the extent of 0.01 to 50 mol %, particularly preferably in the range from 0.1 to 20 mol %. Suitable and preferred comonomers which form the polymer backbone are selected from fluorenes (for example in accordance with EP 842208 or WO 00/22026), spirobifluorenes (for example in accordance with EP 707020, EP 894107 or WO 06/061181), para-phenylenes (for example in accordance with WO 92/18552), carbazoles (for example in accordance with WO 04/070772 or WO 04/113468), thiophenes (for example in accordance with EP 1028136), dihydrophenanthrenes (for example in accordance with WO 05/014689), cis- and trans-indenofluorenes (for example in accordance with WO 04/041901 or WO 04/113412), ketones (for example in accordance with WO 05/040302), phenanthrenes (for example in accordance with WO 05/104264 or WO 07/017,066) or also a plurality of these units. The proportion of these units in total is preferably in the region of at least 50 mol %. The polymers, oligomers and dendrimers may also contain further units, for example hole-transport units, in particular those based on triarylamines, and/or electron-transport units.

Polymers of this type comprising compounds of the general formula I or II can be used for the production of PLEDs, in particular as emitter layer in PLEDs. A polymeric emitter layer can be produced, for example, by coating from solution (spin coating or printing processes).

The compounds according to the invention and the organic electroluminescent devices produced therewith are distinguished by the following surprising advantages over the prior art:

- In contrast to many metal complexes in accordance with the prior art, which undergo partial or complete pyrolytic decomposition on sublimation, the compounds according to the invention have high thermal stability.
- The use of bulky substituents on the aromatic or heteroaromatic ring systems present aggregation of the complexes and thus the formation of excimers or exciplexes to be substantially suppressed.
- Organic electroluminescent devices comprising compounds of the formula I or II as emitting materials have an excellent lifetime.
- Blue-, red- and green-phosphorescent complexes which have an efficient dark-blue, red or even green emission colour and have a long lifetime on use in organic electroluminescent devices are accessible. This is a significant advance over the prior art, since blue-, red- and green-phosphorescent devices were hitherto only accessible with poor colour coordinates and in particular a very poor lifetime.
- The compounds according to the invention, employed in organic electroluminescent devices, result in high efficiencies and steep current-voltage curves at the same time as a low use voltage.

These above-mentioned advantages are not accompanied by an impairment of the other electronic properties.

The invention is explained in greater detail by the following examples, without wishing to restrict it thereby. The person skilled in the art will be able to synthesise further compounds according to the invention without inventive step and employ them in organic electroluminescent devices.

EXAMPLES

The following syntheses are carried out under a protective-gas atmosphere in dried solvents, unless indicated otherwise.

Complex Synthesis (Method A):

A solution of the corresponding imine ligand (4.1 mmol) in 130 ml of acetic acid is added to a solution of 1.7 g of $K_2PtCl_4$ (4.1 mmol) in 130 ml of acetic acid under $N_2$, and the mixture is stirred at 90° C. for 3 days. After filtration, the solid is dried in vacuo and subsequently recrystallised under protective gas.

Complex Synthesis (Method B):

A solution of the corresponding imine ligand (2 mmol) in 20 ml of methanol is added to a solution of 0.57 g of allylpalladium(II) chloride dimer (1 mmol) in 25 ml of MeOH under $N_2$, and the mixture is stirred at 40° C. for 4 days. After filtration, the isolated solid is stirred at 90° C. for 3 days with a further 2 mmol of the corresponding imine ligand in 130 ml of acetic acid. After filtration, the solid is dried in vacuo and subsequently recrystallised under protective gas.

Example 1

Pt Complex (9)

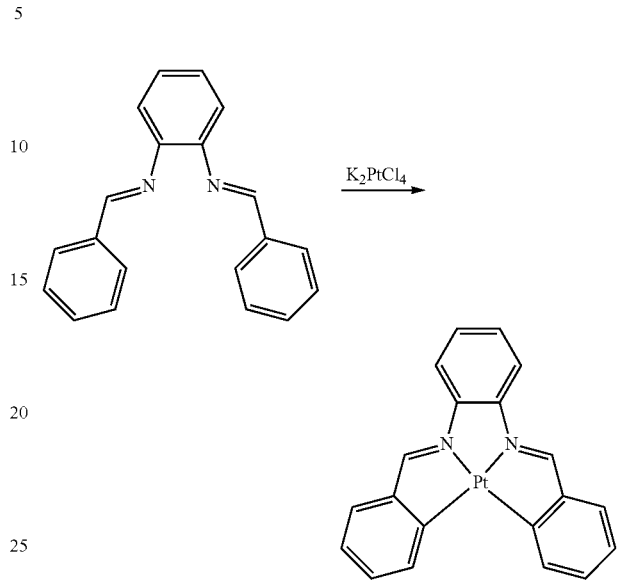

A solution of 11 g (41.5 mmol) of N,N'-dibenzylidene-o-phenylenediamine in 1300 ml of acetic acid is added to a solution of 17.2 g of $K_2PtCl_4$ (41.5 mmol) in 1300 ml of acetic acid under $N_2$, and the mixture is stirred at 90° C. for 3 days. After 72 h, the precipitated solid is washed with cold methanol, dried in vacuo and subsequently recrystallised from absolute EtOH under protective gas, giving 16 g (33.3 mmol) of crystalline solid. The overall yield is 87%.

Example 2

Pt Complex (11)

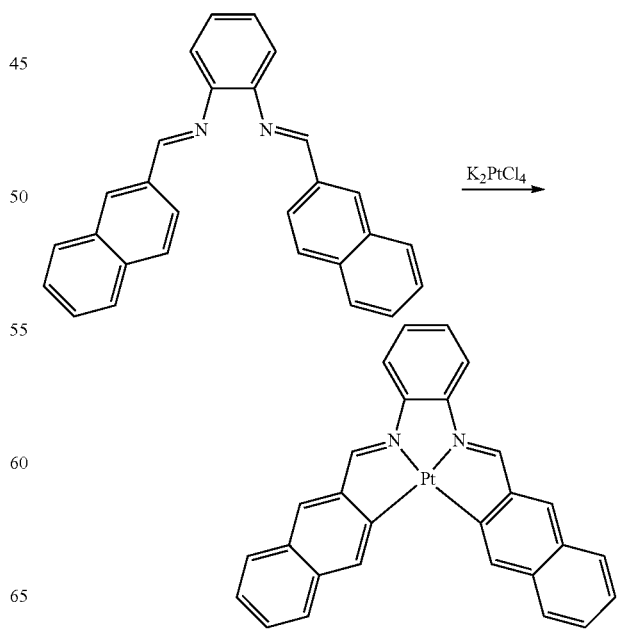

A solution of 15.9 g (41.5 mmol) of N,N'-bis(2-naphthalenylmethylene)-1,2-benzenediimine in 1300 ml of acetic acid is added to a solution of 17.2 g of K$_2$PtCl$_4$ (41.5 mmol) in 1300 ml of acetic acid under N$_2$, and the mixture is stirred at 90° C. for 3 days. After 72 h, the precipitated solid is washed with cold methanol, dried in vacuo and subsequently recrystallised from absolute EtOH under protective gas, giving 19.4 g (33.4 mmol) of crystalline solid. The overall yield is 81%.

Example 3

Pt Complex (20)

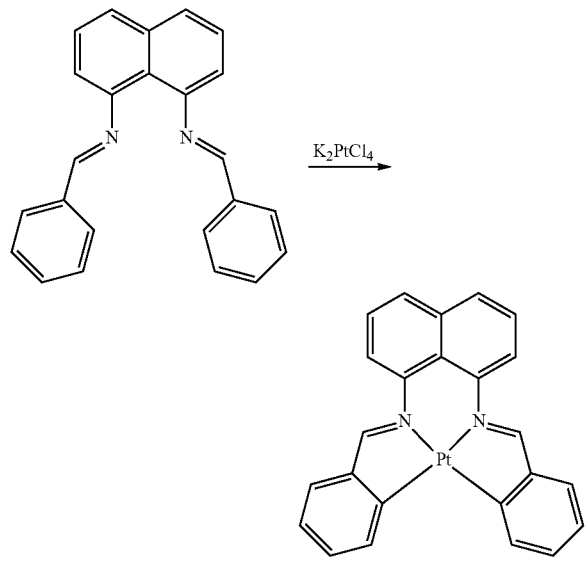

A solution of 12.8 g (41.5 mmol) of N,N'-di(benzylidene)-1,8-diaminonaphthalene in 1300 ml of acetic acid is added to a solution of 17.2 g of K$_2$PtCl$_4$ (41.5 mmol) in 1300 ml of acetic acid under N$_2$, and the mixture is stirred at 90° C. for 3 days. After 72 h, the precipitated solid is washed with cold methanol, dried in vacuo and subsequently recrystallised from absolute EtOH under protective gas, giving 17 g (32.1 mmol) of crystalline solid. The overall yield is 78%.

Example 4

Pt Complex (1)

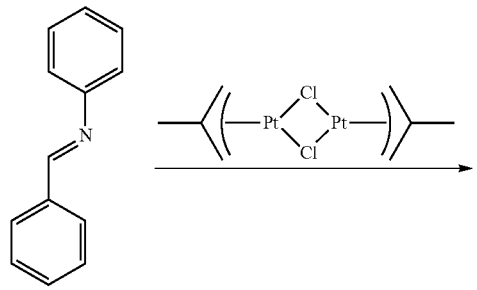

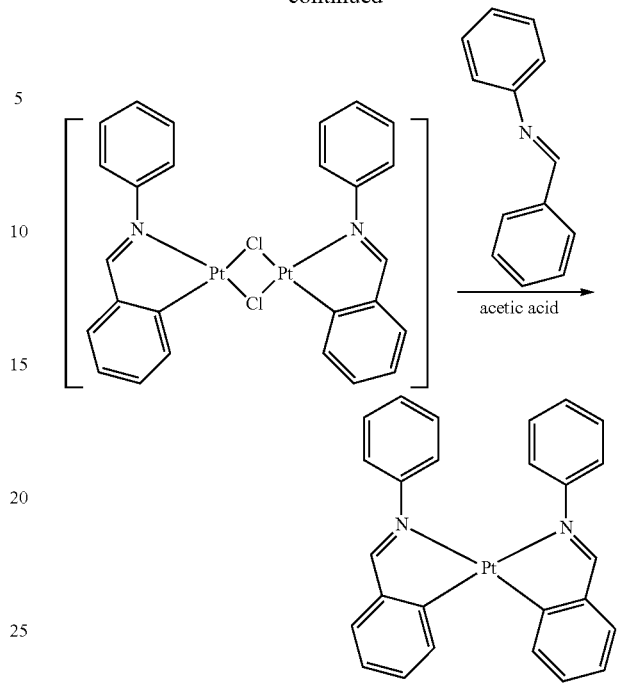

A solution of 2.17 g (12 mmol) of N-phenylbenzaldimine in 120 ml of methanol is added to a solution of 4.4 g (4.25 mmol) of bis(methylallylplatinum(II) chloride) in 150 ml of MeOH, and the mixture is stirred at 40° C. for 4 days. After filtration, the isolated solid is stirred at 90° C. for 3 days with 2.17 g (12 mmol) of N-phenylbenzaldimine in 780 ml of acetic acid. After filtration, the solid is dried in vacuo and subsequently recrystallised under protective gas, giving 5.4 g (9.4 mmol) of crystalline solid. The overall yield is 80%.

Example 5

Production and Characterisation of Organic Electroluminescent Devices

Electroluminescent devices according to the invention can be produced as described, for example, in WO 05/003253. The results for various OLEDs are compared here. The basic structure, the materials used, the degree of doping and the layer thicknesses thereof are identical for better comparability.

The first device example describes a comparative standard in accordance with the prior art, in which the emission layer consists of the host material spiro-ketone and the guest material (dopant) Ir(ppy)$_3$ or a compound according to the invention. Furthermore, OLEDs of various structures are described, the host material is in each case spiro-ketone. OLEDs having the following structure are produced analogously to the above-mentioned general process:

Hole-injection layer (HIL) 20 nm of 2,2',7,7'-tetrakis(di-para-tolylamino)spiro-9,9'-bifluorene Hole-transport layer (HTL) 20 nm of NPB (N-naphthyl-N-phenyl-4,4'-diaminobiphenyl)

Emission layer (EML) 40 nm of host: spiro-ketone (SK) (bis(9,9'-spirobifluoren-2-yl) ketone)

Dopant: Ir(ppy)$_3$ (10% doping, vapour-deposited; synthesised in accordance with WO 03/0068526) or compound according to the invention Electron conductor (ETL) 20 nm of AlQ$_3$ (tris(quinolinato)aluminium(III))

Cathode 1 nm of LiF, 150 nm of Al on top.

The structures of Ir(ppy)$_3$ and spiro-ketone are depicted below for clarity:

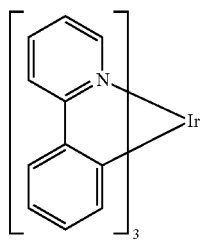

Ir(PPy)$_3$

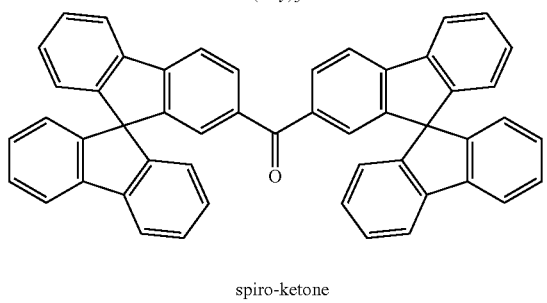

spiro-ketone

The compounds according to the invention used are depicted below:

Example 1

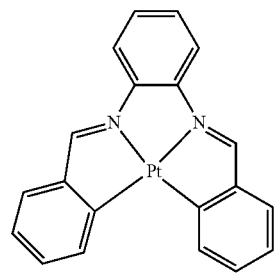

Example 2

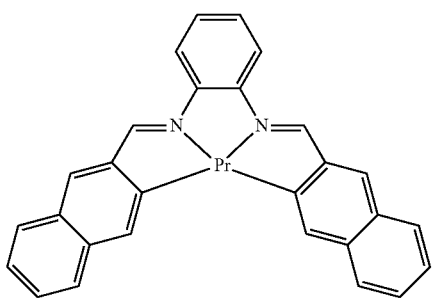

These as yet unoptimised OLEDs are characterised by standard methods; for this purpose, the electroluminescence spectra, the efficiency (measured in cd/A) as a function of the luminance, calculated from current-voltage-luminance characteristic lines (IUL characteristic lines), and the lifetime are determined. Table 2 shows the results of the device measurement. The devices comprising the compounds according to the invention exhibit an improved lifetime with comparable efficiency.

TABLE 2

Device results with spiro-ketone as host material and with Ir(ppy)$_3$ or compounds according to the invention as dopant

| Ex. | EML | Max. efficiency [cd/A] | Voltage [V] at 1000 cd/m$^2$ | CIE (x, y) | Lifetime, initial luminance 1000 cd/m$^2$ [h] |
|---|---|---|---|---|---|
| 5a | SK: 10% Ir(ppy)$_3$ | 30 | 4.4 | 0.38/0.57 | 7700 |
| 5b | SK: 10% Ex. 1 | 28 | 4.2 | 0.31/0.60 | 12000 |
| 5c | SK: 10% Ex. 2 | 35 | 4.1 | 0.34/0.60 | 11000 |

The invention claimed is:

1. A compound of formula II

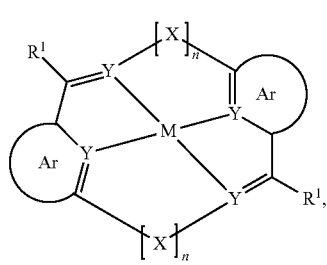

formula II wherein

M is Pt$^{2+}$,

Ar is, identically or differently on each occurrence, an aromatic ring system having 5 to 10 aromatic ring atoms, which may be substituted by a plurality of radicals R, Y is, identically or differently on each occurrence, C or N, with the proviso that always two C atoms are part of Ar and two N atoms are always bonded to the metal, X is, identically or differently on each occurrence, a divalent group selected from

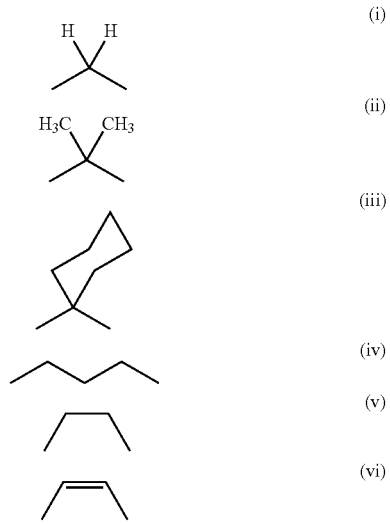

-continued
(vii) 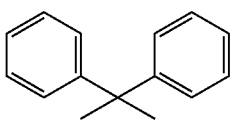
(viii) 
(ix) 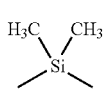
(x) 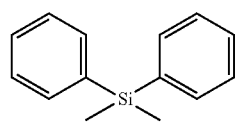
(xi) 
(xii) 
(xiii) 
(xiv) 
(xv) 
(xvi) 
(xvii) 
(xviii) 
(xix) 
(xx) 
or combinations thereof, or an aromatic or heteroaromatic ring system having 5 to 15 aromatic ring atoms selected from
(xxi) 
-continued
(xxii) 
(xxiii) 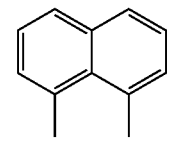
(xxiv) 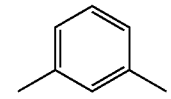
(xxv) 
(xxvi) 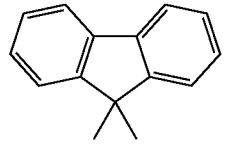
(xxvii) 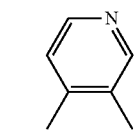
(xxviii) 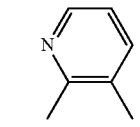
(xxix) 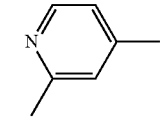
(xxx) 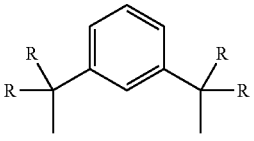
(xxxi) 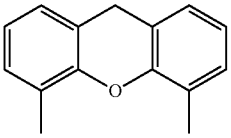
(xxxii) 

which is optionally substituted by one or more radicals R, or combinations thereof, R is, identically or differently on each occurrence, $N(Ar^1)_2$, CN, a straight-chain alkyl group having 1 to 3 C atoms, or an aromatic or heteroaromatic ring system having 5 to 10 aromatic ring atoms, which may in each case be substituted by one or more radicals $R^2$, $R^1$ is, identically or differently on each occurrence, H, D, CN, an alkyl group having 1 to 10 C atoms, or an aromatic or heteroaromatic ring system having 5 to 10 aromatic ring atoms, which may in each case be substituted by one or more radicals $R^2$, $R^2$ is, identically or differently on each occurrence, H, F, CN or an aliphatic aromatic and/or heteroaromatic hydrocarbon radical having 1 to 10 C atoms, where two or more substituents $R^2$ may also form a mono- or polycyclic aliphatic or aromatic ring system with one another, and $Ar^1$ is, identically or differently on each occurrence, an aromatic or heteroaromatic ring system having 5 to 40 aromatic ring atoms, which may be substituted by one or more non-aromatic radicals R, n is on each occurrence, identically or differently, 0 or 1, where, for n=0, a hydrogen or a radical R or Ar is bonded instead of the X concerned.

2. A compound of formula II

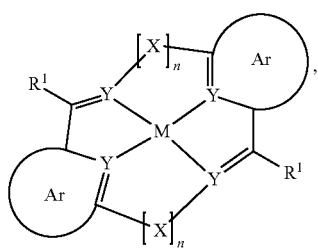

formula II wherein

M is $Pt^{2+}$,

Ar is, identically or differently on each occurrence, an aromatic or heteroaromatic ring system having 5 to 10 aromatic ring atoms, which may be substituted by a plurality of radicals R, Y is, identically or differently on each occurrence, C or N, with the proviso that always either two C atoms and two N atoms are always bonded to the metal, X is, identically or differently on each occurrence, a divalent group selected from

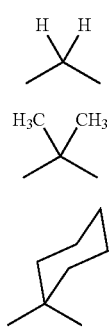

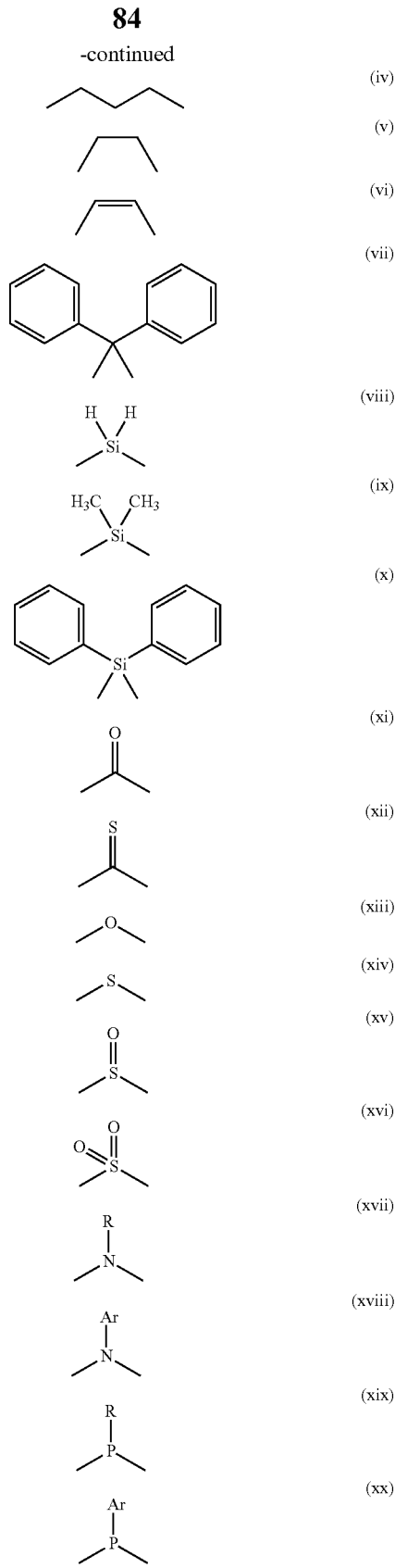

or combinations thereof, or an aromatic or heteroaromatic ring system having 5 to 15 aromatic ring atoms, selected from

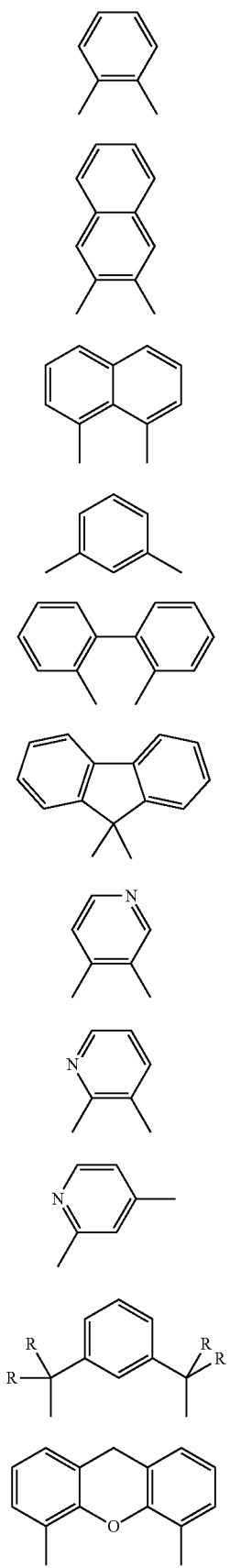

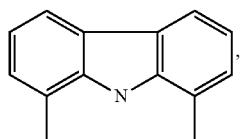

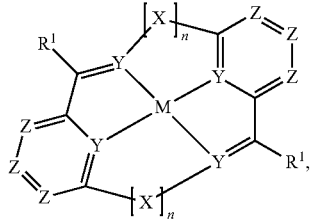

which is optionally substituted by one or more radicals R, or combinations thereof, R is, identically or differently on each occurrence, $N(Ar^1)_2$, CN, a straight-chain alkyl group having 1 to 3 C atoms, or an aromatic or heteroaromatic ring system having 5 to 10 aromatic ring atoms, which may in each case be substituted by one or more radicals $R^2$, $R^1$ is, identically or differently on each occurrence, H, D, CN, an alkyl group having 1 to 10 C atoms, or an aromatic or heteroaromatic ring system having 5 to 10 aromatic ring atoms, which may in each case be substituted by one or more radicals $R^2$, $R^2$ is, identically or differently on each occurrence, H, F, CN or an aliphatic, aromatic and/or heteroaromatic hydrocarbon radical having 1 to 10 C atoms, where two or more substituents $R^2$ may also form a mono- or polycyclic aliphatic or aromatic ring system with one another, and $Ar^1$ is, identically or differently on each occurrence, an aromatic or heteroaromatic ring system having 5 to 40 aromatic ring atoms, which may be substituted by one or more non-aromatic radicals R, n is on each occurrence, identically or differently, 0 or 1, with the proviso that at least one n=1, and where, for n=0, a hydrogen or a radical R or Ar is bonded instead of the X concerned.

3. The compound of 2, wherein the group Ar is selected from benzene, naphthalene, pyridine, pyrimidine, pyrazine pyridazine, quinoline, isoquinoline, furan, thiophene, pyrrole, benzofuran, benzothiophene and indole.

4. The compound of 2, wherein said compound is a compound of formula IV:

formula IV wherein
Z is, identically or differently on each occurrence, CR or N.

5. The compound of claim 4, wherein Z is CR.

6. An oligomer, polymer or dendrimer comprising one or more compounds of 2, wherein one or more bonds are present from the compounds of the formula II to the polymer, oligomer or dendrimer.

7. A process for preparing the compound of claim 2, comprising the step of reacting free ligand with a corresponding metal salt to give the complex.

8. A layer comprising at least one compound of 2.

9. An organic electronic device comprising one or more compounds of 2.

10. The organic electronic device of claim 9, wherein said organic electronic device is an organic electroluminescence device and the compound of formula II is employed as emitting compound in an emitting layer or as charge-transport compound in a charge-transport layer or charge injection layer.

11. The organic electronic device of claim 9, wherein said organic electronic device is a organic electroluminescent device, a polymeric electroluminescent device, an organic integrated circuit, an organic field-effect transistor, an organic thin-film transistor, an organic light-emitting transistor, an organic solar cell, an organic optical detector, an organic photoreceptor, an organic field-quench device, a light-emitting electrochemical cell, or a organic laser diode.

12. A compound of formula I

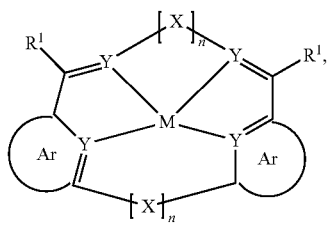

formula I wherein
M is Pt$^{2+}$,
Ar is, identically or differently on each occurrence, an aromatic or heteroaromatic ring system having 5 to 10 aromatic ring atoms, which may be substituted by a plurality of radicals R,
Y is, identically or differently on each occurrence, C or N, with the proviso that always either two C atoms and two N atoms are always bonded to the metal,
X is, identically or differently on each occurrence, a divalent group selected from

 (i)

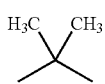 (ii)

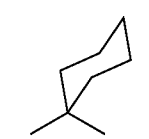 (iii)

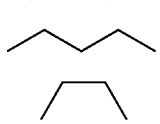 (iv)

 (v)

(vi)

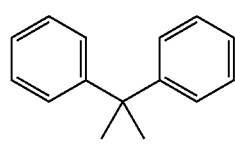 (vii)

 (viii)

 (ix)

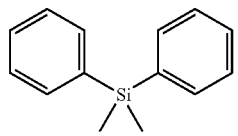 (x)

 (xi)

 (xii)

 (xiii)

 (xiv)

 (xv)

 (xvi)

 (xvii)

 (xviii)

 (xix)

 (xx)

or combinations thereof, or an aromatic or heteroaromatic ring system having 5 to 15 aromatic ring atoms, selected from

 (xxii)

-continued

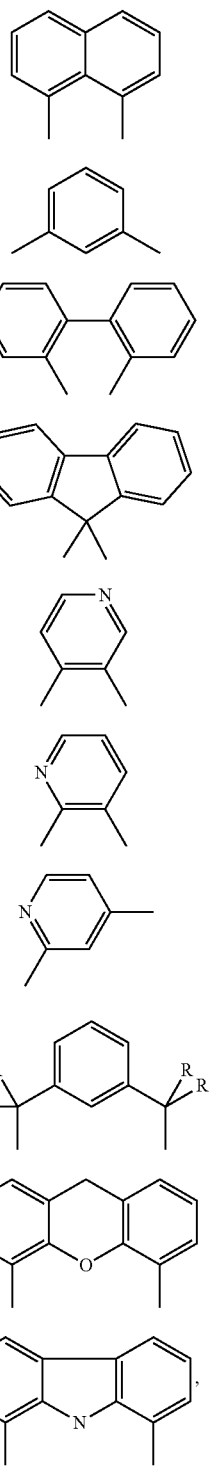

(xxiii)

(xxiv)

(xxv)

(xxvi)

(xxvii)

(xxviii)

(xxix)

(xxx)

(xxxi)

(xxxii)

which is optionally substituted by one or more radicals R, or combinations thereof, R is, identically or differently on each occurrence, $N(Ar^1)_2$, CN, a straight-chain alkyl group having 1 to 3 C atoms, or an aromatic or heteroaromatic ring system having 5 to 10 aromatic ring atoms, which may in each case be substituted by one or more radicals $R^2$, $R^1$ is, identically or differently on each occurrence, H, D, CN, an alkyl group having 1 to 10 C atoms, or an aromatic or heteroaromatic ring system having 5 to 10 aromatic ring atoms, which may in each case be substituted by one or more radicals $R^2$, $R^2$ is, identically or differently on each occurrence, H, F, CN or an aliphatic, aromatic and/or heteroaromatic hydrocarbon radical having 1 to 10 C atoms, where two or more substituents $R^2$ may also form a mono- or polycyclic aliphatic or aromatic ring system with one another, and $Ar^1$ is, identically or differently on each occurrence, an aromatic or heteroaromatic ring system having 5 to 40 aromatic ring atoms, which may be substituted by one or more non-aromatic radicals R, n is on each occurrence, identically or differently, 0 or 1, with the proviso that exactly one n=1, and where, for n=0, a hydrogen or a radical R or Ar is bonded instead of the X concerned.

13. The compound of 12, wherein the group Ar is selected from benzene, naphthalene, pyridine, pyrimidine, pyrazine, quinoline, isoquinoline, furan, thiophene, pyrrole, benzofuran, benzothiophene and indole.

14. The compound of 12, wherein said compound is a compound of formula III:

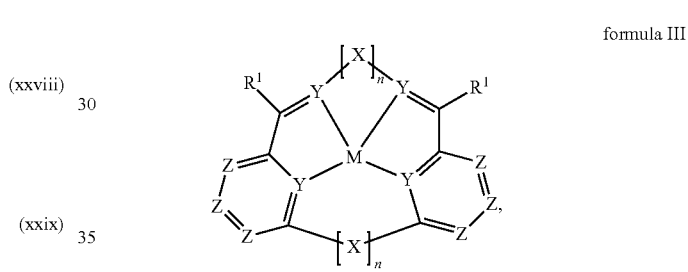

formula III wherein

Z is identically or differently on each occurrence, CR or N.

15. The compound of claim 14, wherein Z is CR.

16. An oligomer, polymer or dendrimer comprising one or more compounds of 12, wherein one or more bonds are present from the compounds of the formula I to the polymer, oligomer or dendrimer.

17. A process for preparing the compound of claim 12, comprising the step of reacting free ligand with a corresponding metal salt to give the complex.

18. A layer comprising at least one compound of 12.

19. An organic electronic device comprising one or more compounds of 12.

20. The organic electronic device of claim 19, wherein said organic electronic device is an organic electroluminescence device and the compound of formula I is employed as emitting compound in an emitting layer or as charge-transport compound in a charge-transport layer or charge injection layer.

21. The organic electronic device of claim 19, wherein said organic electronic device is a organic electroluminescent device, a polymeric electroluminescent device, an organic integrated circuit, an organic field-effect transistor, an organic thin-film transistor, an organic light-emitting transistor, an organic solar cell, an organic optical detector, an organic photoreceptor, an organic field-quench device, a light-emitting electrochemical cell, or a organic laser diode.

* * * * *